US012613177B2

(12) United States Patent
Hernandez et al.

(10) Patent No.: US 12,613,177 B2
(45) Date of Patent: Apr. 28, 2026

(54) SYSTEMS AND METHODS FOR DETECTING PARTICLES OF INTEREST USING MULTI-MODEL SPECTRAL ANALYSIS

(71) Applicant: Hyperspectral Corp., Alexandria, VA (US)

(72) Inventors: Sarah Rachel Hernandez, Austin, TX (US); Matthew Theurer, Alexandria, VA (US)

(73) Assignee: HyperSpectral Corp., Alexandria, VA (US)

( * ) Notice: Subject to any disclaimer, the term of this patent is extended or adjusted under 35 U.S.C. 154(b) by 106 days.

(21) Appl. No.: 18/495,726

(22) Filed: Oct. 26, 2023

(65) Prior Publication Data

US 2024/0142359 A1     May 2, 2024

Related U.S. Application Data

(60) Provisional application No. 63/381,249, filed on Oct. 27, 2022.

(51) Int. Cl.
*G01N 15/0205* (2024.01)
*G01N 15/00* (2024.01)
(Continued)

(52) U.S. Cl.
CPC ..... *G01N 15/0211* (2013.01); *G01N 15/0205* (2013.01); *G01N 15/0656* (2013.01);
(Continued)

(58) Field of Classification Search
CPC ........... G01N 15/0211; G01N 15/0205; G01N 15/0656; G01N 35/00732; G01N 35/00871; G01N 15/075; G01N 2015/03; G01N 2035/00752; G01N 2035/00881; G16B 40/10; G16H 10/40
See application file for complete search history.

(56) References Cited

U.S. PATENT DOCUMENTS

2018/0232883 A1* 8/2018 Sethi ....................... G16H 30/40
2020/0096434 A1* 3/2020 Deran ....................... G06N 3/08
(Continued)

OTHER PUBLICATIONS

International Application No. PCT/US2023/077978, International Search Report and the Written Opinion, dated Mar. 5, 2024, 10 pages.

*Primary Examiner* — Dominic J Bologna

(57) ABSTRACT

An example method includes receiving data that includes a set of spectral metrics from interactions of electromagnetic radiation with a sample. A first trained model and a second trained model is applied to at least one of the set of spectral metrics and a set of values based on the set of spectral metrics to obtain a first result and a second result. Based on at least one of the first result and the second result, either a positive particle of interest detection or a negative particle of interest detection for at least one of first particles of interest, a first type of the first particles of interest, and a second type of the first particles of interest for the sample is determined. A particle of interest detection notification that indicates either the positive particle of interest detection or the negative particle of interest detection is generated and provided.

20 Claims, 19 Drawing Sheets

(51) Int. Cl.
  G01N 15/06 (2024.01)
  G01N 15/075 (2024.01)
  G01N 35/00 (2006.01)
  G16B 40/10 (2019.01)
  G16H 10/40 (2018.01)

(52) U.S. Cl.
  CPC . G01N 35/00732 (2013.01); G01N 35/00871 (2013.01); G16B 40/10 (2019.02); G16H 10/40 (2018.01); *G01N 2015/03* (2013.01); *G01N 15/075* (2024.01); *G01N 2035/00752* (2013.01); *G01N 2035/00881* (2013.01)

(56) References Cited

U.S. PATENT DOCUMENTS

| | | | | |
|---|---|---|---|---|
| 2021/0106231 A1* | 4/2021 | Radhakrishnan | ...... | G01N 21/31 |
| 2021/0293625 A1* | 9/2021 | Gao | ........................ | G01J 5/601 |
| 2022/0160265 A1* | 5/2022 | Sankhala | ............... | G16H 40/63 |
| 2022/0222798 A1 | 7/2022 | Panigrahi et al. | | |
| 2023/0393078 A1* | 12/2023 | Pruneri | ............. | G01N 21/8851 |

* cited by examiner

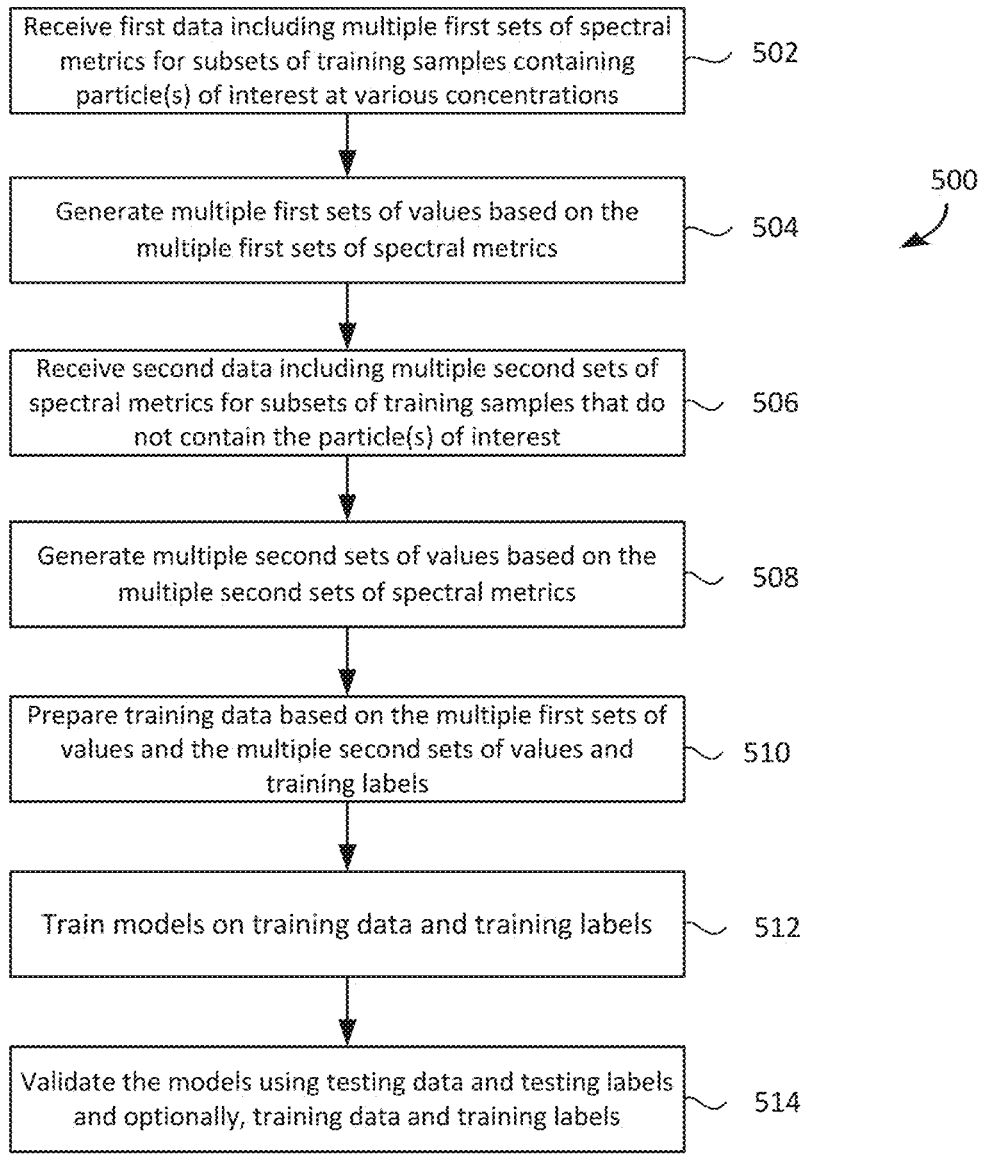

Receive first data including multiple first sets of spectral metrics for subsets of training samples containing particle(s) of interest at various concentrations — 502

Generate multiple first sets of values based on the multiple first sets of spectral metrics — 504

Receive second data including multiple second sets of spectral metrics for subsets of training samples that do not contain the particle(s) of interest — 506

Generate multiple second sets of values based on the multiple second sets of spectral metrics — 508

Prepare training data based on the multiple first sets of values and the multiple second sets of values and training labels — 510

Train models on training data and training labels — 512

Validate the models using testing data and testing labels and optionally, training data and training labels — 514

| Color(s) | Size(s) (nm) | Feature Name (nm) | Importance |
|---|---|---|---|
| Red | 50 | 537 | 0.39 |
| | | 466 | 0.24 |
| | | 320 | 0.12 |
| | | 467 | 0.11 |
| | | 344 | 0.05 |
| | 500 | 562 | 0.48 |
| | | 605 | 0.12 |
| | | 558 | 0.08 |
| | | 328 | 0.07 |
| | | 563 | 0.06 |
| | 1000 | 328 | 0.97 |
| | | 327 | 0.03 |
| Red | 50/500/1000 | 393 | 0.08 |
| | | 537 | 0.05 |
| | | 422 | 0.05 |
| | | 994 | 0.04 |
| | | 728 | 0.03 |
| Green | 50 | 451 | 0.37 |
| | | 528 | 0.12 |
| | | 320 | 0.12 |
| | | 325 | 0.11 |
| | | 917 | 0.1 |
| | 500 | 660 | 0.43 |
| | | 924 | 0.19 |
| | | 698 | 0.11 |
| | | 320 | 0.06 |
| | | 926 | 0.05 |
| | 1000 | 332 | 0.38 |
| | | 328 | 0.31 |
| | | 402 | 0.06 |
| | | 327 | 0.06 |
| | | 1014 | 0.05 |
| Green | 50/500/1000 | 1043 | 0.12 |
| | | 828 | 0.12 |
| | | 466 | 0.09 |
| | | 1038 | 0.07 |
| | | 1042 | 0.04 |
| Red, Green, Red/Green Mix | 50/500/1000 | 867 | 0.04 |
| | | 398 | 0.02 |
| | | 355 | 0.02 |
| | | 1090 | 0.02 |
| | | 466 | 0.02 |

600

700

750

800

850

| Color | Size | Concentration | Accuracy | Specificity | Sensitivity |
|-------|------|---------------|----------|-------------|-------------|
| Red | 15 | 0 | 0.76 | 0.91 | 0.46 |
| | | 1 | 0.908 | 0.93 | 0.88 |
| | | 2 | 0.485 | 0.814 | 0.1 |
| | | 3 | 0.551 | 0.8 | 0.24 |
| | | 4 | 0.609 | 0.98 | 0 |
| | | 5 | 0.49 | 0.89 | 0 |
| | | 6 | 0.56 | 0.94 | 0 |
| | | 7 | 0.477 | 0.7 | 0.08 |
| | | 8 | 0.846 | 0.975 | 0.64 |
| | | 9 | 0.613 | 0.947 | 0 |
| | | 10 | 0.525 | 0.9 | 0 |
| | | 11 | 0.425 | 0.433 | 0.4 |
| | | 12 | 0.75 | 0.9 | 0.6 |
| | | 13 | 1 | 1 | 1 |
| | | 14 | 1 | 1 | 1 |
| Red | 25 | 5 | 0.54 | 0.68 | 0.26 |
| | | 6 | 0.48 | 0.89 | 0 |
| | | 7 | 0.623 | 0.664 | 0.64 |
| | | 8 | 0.392 | 0.74 | 0 |
| | | 9 | 0.525 | 0.84 | 0 |
| | | 10 | 0.792 | 0.971 | 0.6 |
| | | 11 | 0.985 | 0.991 | 0.98 |
| | | 12 | 0.711 | 0.844 | 0.52 |
| | | 13 | 1 | 1 | 1 |
| Red | 50 | 4 | 0.675 | 0.948 | 0.2 |
| | | 5 | 0.818 | 0.949 | 0.6 |
| | | 6 | 0.549 | 0.789 | 0.3 |
| | | 7 | 0.422 | 0.574 | 0.24 |
| | | 8 | 0.777 | 0.841 | 0.7 |
| | | 9 | 0.869 | 0.871 | 0.88 |
| | | 10 | 1 | 1 | 1 |
| | | 11 | 1 | 1 | 1 |
| | | 12 | 1 | 1 | 1 |
| Red | 500 | 2 | 0.782 | 0.932 | 0.502 |
| | | 3 | 0.677 | 0.86 | 0.24 |
| | | 4 | 0.745 | 0.841 | 0.41 |
| | | 5 | 0.723 | 0.895 | 0.233 |
| | | 6 | 0.945 | 0.964 | 0.92 |
| | | 7 | 0.994 | 0.991 | 1 |
| | | 8 | 1 | 1 | 1 |
| | | 9 | 0.983 | 0.97 | 1 |
| | | 10 | 1 | 1 | 1 |
| Red | 1000 | 1 | 0.846 | 0.93 | 0.701 |
| | | 2 | 0.808 | 0.947 | 0.49 |
| | | 3 | 0.797 | 0.808 | 0.733 |
| | | 4 | 0.817 | 0.919 | 0.523 |
| | | 5 | 0.927 | 0.954 | 0.865 |
| | | 6 | 0.994 | 0.991 | 1 |
| | | 7 | 0.993 | 0.989 | 1 |
| | | 8 | 1 | 1 | 1 |
| | | 9 | 1 | 1 | 1 |

SYSTEMS AND METHODS FOR DETECTING PARTICLES OF INTEREST USING MULTI-MODEL SPECTRAL ANALYSIS

CROSS-REFERENCE TO RELATED APPLICATION

This application claims priority to U.S. Provisional Patent Application No. 63/381,249, filed on Oct. 27, 2022, and entitled "SYSTEMS AND METHODS TO DETECT DEEP SIGNATURE FOR PARTICLES OF INTEREST," which is incorporated in its entirety herein by reference.

FIELD OF THE INVENTION(S)

Embodiments of the present invention(s) are generally related to detecting particle of interests by analyzing spectral metrics, and in particular to detecting particle of interests such as foodborne pathogens, pathogens that infect humans and/or animals, and environmental pathogens, using multi-model spectral analysis.

BACKGROUND

Foodborne illnesses may be caused by consuming food or beverages that are contaminated by pathogens, allergens, foreign particles, or fraudulent ingredients, such as bacteria, toxins produced by bacteria, viruses, parasites, chemicals, foreign material (e.g., metal shavings), and/or the like. The United States Food and Drug Administration (U.S. FDA) estimates that there are approximately 48 million cases of foodborne illness each year in the United States. The U.S. FDA further estimates that 1 in 6 Americans are affected by foodborne illnesses, resulting in 128,000 hospitalizations and 3,000 deaths per year.

Food or beverages (collectively, food) may be contaminated during any stage in the supply chain (e.g., in the field, while undergoing processing at food production or processing facilities (collectively, food processing facilities), or during shipping or transport), distribution, retail, restaurant, or improper storage/handling/expiration at a home. However, the contamination may not be discovered until after people are sickened from consuming the food, which may be due to the fact that food processors cannot wait for test results as they need to ship food to meet shelf-life expectations. Unfortunately, government agencies, such as the U.S. FDA, often declare an outbreak of a foodborne illness and issue recalls of the food suspected of causing the outbreak only after a number of people are sickened.

In addition to the deleterious effects on individual health, there are economic costs to recalls. For example, a food producer or processor (collectively, a food processor) may voluntarily or be required to recall numerous lots of food or entire production runs. Such recalls may sicken many and may tarnish the brand of the food processor, leading to consumer distrust, reduced sales, and large costs for product recalls, legal defense, damage control, and insurance premiums.

Furthermore, during a pandemic and the aftermath, it may be vital to identify infected people. Multiple testing methods have been developed to diagnose viral infections, including polymerase chain reaction (PCR), enzyme-linked immunosorbent assay, immunofluorescent assay, and others. However, these methods are impractical when it comes to wide-scale screening because of lack of speed, lack of accuracy, lack of resources, dependency on foreign supply chains for reagents, and cost. As seen with the COVID-19 pandemic, when attempting to screen large populations, reagent supplies may become depleted, and current testing methodologies may take days to return a result back to a patient. Due to the limited supply of test equipment, testing may be performed on people who actively present symptoms and self-identify. The testing is primarily used to verify the diagnosis.

Relying on a person to present symptoms is a significant challenge for containment because of the reliance on a person's immune system's response to the virus (such as running a fever or developing a persistent dry cough). In the case of COVID-19, infected people may be contagious but asymptomatic during the long incubation period of the virus (e.g., 2-14 days). The long incubation period has made the virus difficult to contain (which may be due in part to long-lead times for diagnosis) and has led governments to take strong action to reduce spread of the virus. These strong actions include orders for long-term shelter-in-place and social distancing.

These problems can be common for many different pathogens, allergens, or harmful agents. There are many bacteria and viruses, for example, which may be asymptomatic for a period of time but may have serious health consequences. Further, many bacteria and viruses may be highly infectious either before or after symptoms appear. Testing for any number of pathogens can be invasive, uncomfortable, and/or painful. In addition, many tests for a specific pathogen may be inaccurate, slow, expensive, or unavailable to the mass population. Moreover, the potency or effectiveness of many compounds (e.g., reagents) used to test pathogens may change due to age, exposure to environmental conditions, and/or improper handling.

Furthermore, environmental hazards such as methane, ethylene, methylene, and other volatile organic compounds (VOCs) may pose risks to human health and environmental health. The detection and mitigation of such environmental hazards may be required by various governmental agencies and/or corporate policies.

Furthermore, a substance or item may become contaminated with or come in contact with another, undesirable, substance. For example, air may become polluted by carbon monoxide. As another example, water may become contaminated with chemicals. Such contaminants may be difficult or impossible for humans to detect with only their innate senses.

SUMMARY

In some aspects, the techniques described herein relate to a non-transitory computer-readable medium including executable instructions, the executable instructions being executable by one or more processors to perform a method, the method including: receiving data, the data including a set of spectral metrics, the data from an apparatus that obtains the set of spectral metrics based on interactions of electromagnetic radiation with a sample; applying a first trained model to at least one of the set of spectral metrics and a set of values based on the set of spectral metrics to obtain a first result, the first trained model trained on a first set of training samples for first particles of interest and a second set of training samples for second particles of interest, the first particles of interest including at least a first type of the first particles of interest and a second type of the first particles of interest; applying a second trained model to at least one of the set of spectral metrics and the set of values to obtain a second result, the second trained model trained on a third set of training samples for the first type of the first particles of interest and a fourth set of training samples for the second type of the first particles of interest; based on at least one of the first result and the second result, determining either a positive particle of interest detection or a negative particle of interest detection for at least one of the first particles of interest, the first type of the first particles of interest, and the second type of the first particles of interest for the sample; generating a particle of interest detection notification that indicates either the positive particle of interest detection or the negative particle of interest detection; and providing the particle of interest detection notification.

In some aspects, the techniques described herein relate to a non-transitory computer-readable medium wherein the sample is at least one of a sample of a food processing byproduct, a sample from a person, and an environmental sample, and at least one of the first particles of interest and the second particles of interest includes at least one of a foodborne pathogen, a pathogen that infects humans or animals, and an environmental particle of interest.

In some aspects, the techniques described herein relate to a non-transitory computer-readable medium, the method further including normalizing each spectral metric in the set of spectral metrics to be between zero, inclusive, and one, inclusive, to obtain the set of values, and wherein applying the first trained model to at least one of the set of spectral metrics and the set of values based on the set of spectral metrics to obtain the first result includes applying the first trained model to the set of values.

In some aspects, the techniques described herein relate to a non-transitory computer-readable medium, the method further including: training a first model on the first set of training samples for the first particles of interest and the second set of training samples for the second particles of interest to obtain the first trained model; and training a second model on the third set of training samples for the first type of the first particles of interest and the fourth set of training samples for the second type of the first particles of interest to obtain the second trained model.

In some aspects, the techniques described herein relate to a non-transitory computer-readable medium wherein at least some training samples of at least one of the first set of training samples, the second set of training samples, the third set of training samples, and the fourth set of training samples correspond to a particular food processing facility, a region that includes multiple food processing facilities, or one or more classes of food processing facilities.

In some aspects, the techniques described herein relate to a non-transitory computer-readable medium wherein spectral metrics in the set of spectral metrics include one of absorbance metrics, transmittance metrics, reflectance metrics, and scattering metrics.

In some aspects, the techniques described herein relate to a non-transitory computer-readable medium wherein at least one of the first result and the second result indicates the positive particle of interest detection if at least one of the first result and the second result meets or exceeds a threshold.

In some aspects, the techniques described herein relate to a non-transitory computer-readable medium wherein the electromagnetic radiation includes at least one of ultraviolet light, visible light, and infrared light.

In some aspects, the techniques described herein relate to a non-transitory computer-readable medium wherein the first trained model includes a first set of trained decision trees, and wherein the second trained model includes a second set of trained decision trees.

In some aspects, the techniques described herein relate to a non-transitory computer-readable medium wherein the first set of training samples includes a first subset of training samples containing the first particles of interest at a first concentration and a second subset of training samples containing the first particles of interest at a second concentration different from the first concentration, and wherein the second set of training samples includes a third subset of training samples containing the second particles of interest at a third concentration and a fourth subset of training samples containing the second particles of interest at a fourth concentration different from the third concentration.

In some aspects, the techniques described herein relate to a method including: receiving data, the data including a set of spectral metrics, the data from an apparatus that obtains the set of spectral metrics based on interactions of electromagnetic radiation with a sample; applying a first trained model to at least one of the set of spectral metrics and a set of values based on the set of spectral metrics to obtain a first result, the first trained model trained on a first set of training samples for first particles of interest and a second set of training samples for second particles of interest, the first particles of interest including at least a first type of the first particles of interest and a second type of the first particles of interest; applying a second trained model to at least one of the set of spectral metrics and the set of values to obtain a second result, the second trained model trained on a third set of training samples for the first type of the first particles of interest and a fourth set of training samples for the second type of the first particles of interest; based on at least one of the first result and the second result, determining either a positive particle of interest detection or a negative particle of interest detection for at least one of the first particles of interest, the first type of the first particles of interest, and the second type of the first particles of interest for the sample; generating a particle of interest detection notification that indicates either the positive particle of interest detection or the negative particle of interest detection; and providing the particle of interest detection notification.

In some aspects, the techniques described herein relate to a method wherein the sample is at least one of a sample of a food processing byproduct, a sample from a person, and an environmental sample, and at least one of the first particles of interest and the second particles of interest includes at least one of a foodborne pathogen, pathogen that infects humans or animals, and an environmental particle of interest.

In some aspects, the techniques described herein relate to a method, further including normalizing each spectral metric in the set of spectral metrics to be between zero, inclusive, and one, inclusive, to obtain the set of values, and wherein applying the first trained model to at least one of the set of spectral metrics and the set of values based on the set of spectral metrics to obtain the first result includes applying the first trained model to the set of values.

In some aspects, the techniques described herein relate to a method, further including: training a first model on the first set of training samples for the first particles of interest and the second set of training samples for the second particles of interest to obtain the first trained model; and training a second model on the third set of training samples for the first type of the first particles of interest and the fourth set of training samples for the second type of the first particles of interest to obtain the second trained model.

In some aspects, the techniques described herein relate to a method wherein the first set of training samples includes a first subset of training samples containing the first particles of interest at a first concentration and a second subset of training samples containing the first particles of interest at a second concentration different from the first concentration, and wherein the second set of training samples includes a third subset of training samples containing the second particles of interest at a third concentration and a fourth subset of training samples containing the second particles of interest at a fourth concentration different from the third concentration.

In some aspects, the techniques described herein relate to a system including at least one processor and memory containing executable instructions, the executable instructions being executable by the at least one processor to: receive data, the data including a set of spectral metrics, the data from an apparatus that obtains the set of spectral metrics based on interactions of electromagnetic radiation with a sample; apply a first trained model to at least one of the set of spectral metrics and a set of values based on the set of spectral metrics to obtain a first result, the first trained model trained on a first set of training samples for first particles of interest and a second set of training samples for second particles of interest, the first particles of interest including at least a first type of the first particles of interest and a second type of the first particles of interest; apply a second trained model to at least one of the set of spectral metrics and the set of values to obtain a second result, the second trained model trained on a third set of training samples for the first type of the first particles of interest and a fourth set of training samples for the second type of the first particles of interest; based on at least one of the first result and the second result, determine either a positive particle of interest detection or a negative particle of interest detection for at least one of the first particles of interest, the first type of the first particles of interest, and the second type of the first particles of interest for the sample; generate a particle of interest detection notification that indicates either the positive particle of interest detection or the negative particle of interest detection; and provide the particle of interest detection notification.

In some aspects, the techniques described herein relate to a system wherein the sample is at least one of a sample of a food processing byproduct, a sample from a person, and an environmental sample, and at least one of the first particles of interest and the second particles of interest includes at least one of a foodborne pathogen, a pathogen that infects humans or animals, and an environmental particle of interest.

In some aspects, the techniques described herein relate to a system, the executable instructions being further executable by the at least one processor to normalize each spectral metric in the set of spectral metrics to be between zero, inclusive, and one, inclusive, to obtain the set of values, and wherein the executable instructions to apply the first trained model to at least one of the set of spectral metrics and the set of values based on the set of spectral metrics to obtain the first result includes executable instructions being executable by the at least one processor to apply the first trained model to the set of values.

In some aspects, the techniques described herein relate to a system, the executable instructions being further executable by the at least one processor to: train a first model on the first set of training samples for the first particles of interest and the second set of training samples for the second particles of interest to obtain the first trained model; and train a second model on the third set of training samples for the first type of the first particles of interest and the fourth set of training samples for the second type of the first particles of interest to obtain the second trained model.

In some aspects, the techniques described herein relate to a system wherein the first set of training samples includes a first subset of training samples containing the first particles of interest at a first concentration and a second subset of training samples containing the first particles of interest at a second concentration different from the first concentration, and wherein the second set of training samples includes a third subset of training samples containing the second particles of interest at a third concentration and a fourth subset of training samples containing the second particles of interest at a fourth concentration different from the third concentration.

BRIEF DESCRIPTION OF THE DRAWINGS

FIG. 5 is a flowchart showing a method for training machine learning or artificial intelligence models for detecting particle of interests in some embodiments.

FIG. 9 is a table showing results for light that passed through one or more samples containing microspheres of different sizes at different concentrations in some embodiments.

Throughout the drawings, like reference numerals will be understood to refer to like parts, components, and structures.

DETAILED DESCRIPTION

Figure 1A:
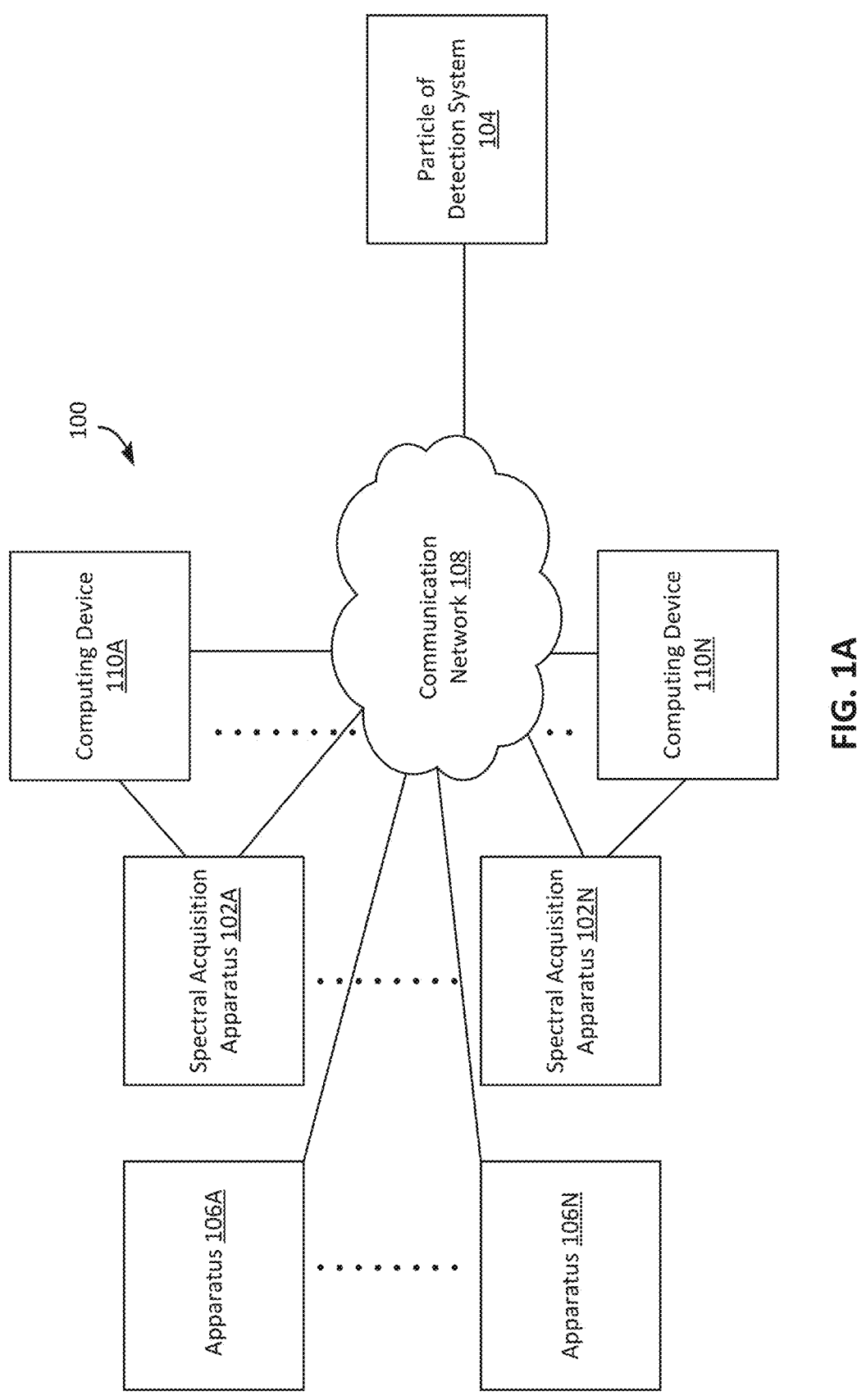
FIG. 1A depicts an example particle of interest detection environment in some embodiments.

A government agency such as the U.S. FDA may not declare a foodborne illness outbreak until after a large number of persons have been sickened and/or if a producer receives a positive result. Before declaring the outbreak, the government agency may have to perform an investigation to determine the food that is causing the outbreak, which may be difficult to do and/or take significant time. If the government agency is able to determine the food, testing for foodborne pathogens has to be performed to identify the particular foodborne pathogen responsible for the foodborne illnesses. The investigation and testing may take a large amount of time, during which more persons may be affected by the contaminated food. One reason for the large amount of time is that it may take approximately 42 hours to approximately 132 hours to obtain test results confirming a foodborne pathogen.

In various embodiments, systems and methods discussed herein may enable early detection of foodborne pathogens during food farming, harvest, production or processing (collectively, food processing) across the entire supply chain (farm to fork). The systems may utilize spectral acquisition apparatuses, which may be or include device that obtains and/or generates spectral metrics, such as spectrometers, spectrophotometers, or thermal emissions spectrometers, or other electromagnetic sources and detectors. The spectral acquisition apparatuses may obtain and/or generate spectral metrics acquired by causing and/or detecting electromagnetic radiation interacting with water, environmental surfaces/spaces, preparation surfaces, drains, food, or any other zones as defined by government agencies (e.g., the U.S. FDA) used or produced by food processing apparatuses. The spectral acquisition apparatuses may transmit the spectral metrics to a particle of interest detection system that utilizes one or more computing systems containing machine learning (ML) and/or artificial intelligence (AI) models to detect evidence of foodborne pathogens from the spectral metrics. The particle of interest detection system may provide results to personnel working in food processing facilities, farmers, distributors, retail, or the household. In the event of a positive detection of a foodborne pathogen, the food may be immediately quarantined and start remedial measures, such as cleaning food processing equipment, discarding contaminated food, and/or performing additional testing or detection to determine root cause and corrective action.

Such early detection of foodborne pathogens allows food processors to identify contaminated food prior to shipping the food out to wholesalers, distributors, retailers, and/or consumers. This early detection may save food processors the costs of recalling food, which may be significant. In addition, early detection may prevent or reduce the occurrence of foodborne illness outbreaks, which may prevent or reduce illnesses, hospitalizations, and deaths.

In various embodiments, the systems and methods described herein are applicable to detect a wide variety of foodborne pathogens that cause foodborne illnesses. Such foodborne pathogens include norovirus, *Salmonella* (non-typhoidal), *Clostridium perfringens, Campylobacter, Staphylococcus aureus, Toxoplasma gondii, Escherichia coli (E. coli), Clostridium botulinum, Cryptosporidium, Cyclospora*, hepatitis A virus, *Shigella, Yersinia*, and *Listeria monocytogenes (Listeria)*, among many others. The particle of interest detection systems may train one or more ML and/or AI models for each foodborne pathogen. Upon receiving spectral metrics from spectral acquisition apparatuses, the particle of interest detection systems may apply the trained machine learning and/or AI models to the spectral metrics. In this way, the particle of interest detection systems may be able to detect multiple particle of interests from spectral metrics of a single sample of a food processing byproduct, rather than using multiple assays and reagents to test particles of interest. One advantage of some embodiments of the systems and methods described herein is that they may decrease the Limit of Detection (LOD) from the Classical Limit of Detection (cLOD) of the spectral analysis equipment, which is limited by physics, to the machine learning limit of detection (mlLOD) that may be one to two orders of magnitude lower than the cLOD. Current detection technology requires the sample to be enriched and incubated in order to stimulate growth/replication in order to detect. The proposed technology reduces the enrichment and incubation time and cost due to the lower LOD (mlLOD) that are capable of detecting very low concentrations of organisms without the need for enrichment/incubation.

In various embodiments, the spectral acquisition apparatuses may be or include spectrometers or other spectral analysis technology, such as commercially available spectrometers or customized UV/VIS/NIR/MWIR/LWIR sensors that are capable of communicating with the particles of interest detection system or are couplable to digital devices capable of communicating with the particles of interest detection system. Food processors may widely deploy the spectral acquisition apparatuses at food processing facilities to detect foodborne pathogens in their food processing. The particles of interest detection systems and associated methods described herein, because they provide more accurate results more quickly and economically than other systems and methods, are broadly applicable to any location where food is processed, such as farms, food processing facilities, packaging facilities, distributors, restaurants, grocery stores, homes, and other locations. Accordingly, the particles of interest detection systems and associated methods described herein may provide significant benefits to farmers, food processors, distributors, restaurant operators, grocery store operators, households, consumers, and others (e.g., any entity in the farm-to-fork supply chain).

The particles of interest detection systems and associated methods, due to the ability to perform rapid and continuous testing of foods, also allow for food processors to quarantine food that may be contaminated by particles of interests prior to shipping out such food. For example, a food processor, upon detection of a foodborne pathogen during a particular food processing run, may be able to quarantine food processed during that run or food processed after the last "clean" test prior to shipping out that food. The food processor may then test the food (e.g., using laboratory tests) to confirm the presence of foodborne pathogens. The food processor may also be able to clean food processing equipment and/or parts of the food processing facility to prevent or reduce contamination of further food. The food processor may then retest food processing byproducts and/or equipment for contamination. As a result, the food processor may confirm that the machinery and/or byproducts are "clean" (e.g., without detected foodborne pathogens) before returning to food processing.

Accordingly, food processors may be able to reduce economic costs associated with foodborne illness outbreaks (and lower food recall insurance premiums due to significantly lower risk). Furthermore, effects on individual health and/or public health may be avoided or reduced by the deployment of the particle of interest detection systems and associated methods described herein.

The particle of interest detection systems and associated methods described herein may also aid food processors (and all other entities in the food supply chain from "farm to fork" in complying with food safety laws and regulations, such as those promulgated by government agencies such as the U.S. FDA.

The particle of interest detection systems and associated methods may also be utilized to detect other particles, allergens, contaminants, or pollutants that can harm human health, human safety, and/or the environment. Accordingly, the particle of interest detection systems and associated methods described herein may also aid community water systems and/or other water suppliers with complying with water quality standards, such as those promulgated by government agencies such as the U.S. Environmental Protection Agency, FDA (for pharmaceuticals), or semiconductor industry associations specifying water quality.

In various embodiments, the particle of interest detection systems and associated methods discussed herein may enable early detection of persons infected with SARS-CoV-2 (or other diseases) prior to those persons presenting symptoms. In one example, persons may provide samples, obtained from saliva, nasal, skin, or other swabs, and/or breath. A spectral acquisition apparatus may perform spectrometer scans of the samples and transmit such scans to particle of interest detection systems for processing. The particle of interest detection systems may apply machine learning algorithms to detect pathogens (e.g., SARS-CoV-2 virions) or other harmful diseases or contamination in the samples. The particle of interest detection systems may then transmit results to the spectral acquisition apparatuses and/or to personal devices of the persons who gave samples. The entire process may return results quickly (e.g., within seconds or minutes), which is a significant improvement over the time it takes to obtain results from PCR, antigen, or other biological tests. Because results can be obtained quickly, infected individuals can be quickly identified, and such individuals may take appropriate measures to prevent the spread to others and seek timely medical care.

The spectral acquisition apparatuses may be or include spectrometers and/or spectrophotometers. The spectrometers may be commercially available optical spectrometers that are capable of communicating with the particle of interest detection systems or are couplable to digital devices capable of communicating with the particle of interest detection systems. As such, the spectral acquisition apparatuses may be widely distributed across geographies and deployed to locations where screening and/or detection of persons infected with SARS-CoV-2 (and/or other communicable diseases) is important. Such locations may include popular entertainment venues (e.g., concert halls), medical facilities (e.g., hospitals), business sites of common carriers (e.g., airports and train stations), and the like. As the particle of interest detection systems may provide results quickly, the screening and/or detection of concert attendees, patients, medical personnel and visitors, travelers and others may be performed rapidly without unduly interfering with the movement of persons into and out of such locations.

For example, individuals in concert sound and stage crews may wish to know of a SARS-CoV-2 infection as soon as possible. This is because such individuals may interact with musicians who must perform or risk significant financial losses. The particle of interest detection systems as described herein, because they can provide quick results, and can provide them accurately and repeatedly, may allow for rapid identification of infected individuals. Accordingly, the particle of interest detection systems can reduce disruptions to concerts and other musical events.

More generally, the particle of interest detection systems and associated methods described herein, because they provide more accurate results more quickly and potentially more economically than PCR, enzyme-linked immunosorbent assay, immunofluorescent assay, and other biological testing methods, may be broadly applicable to any location, event, or circumstances where it is desirable to rapidly identify infected individuals and potentially quarantine them. Accordingly, the particle of interest detection systems and associated methods described herein may reduce social and/or economic disruptions, which may provide significant health and economic benefits to individuals, organizations, and governments. Rapid, low cost, reagent free, and digital spectral test results has the ability to quickly contain the spread of new diseases and/or biological agents that may cause harm to humans.

While detection of SARS-CoV-2 virions may be discussed herein, it will be appreciated that the particle of interest detection systems may detect other pathogens, such as, but not limited to, human immunodeficiency virus (HIV) virions, the various strains of influenza virus virions, and/or the like in addition to or as an alternative. Furthermore, the particle of interest detection systems may detect chemical or protein composition from a number of sources. As such, some of the methods and systems described herein may be applied to food composition analysis, chemical composition analysis, water purity, and the like.

While systems described herein may refer to detection of pathogens, it will be appreciated that the systems described herein may detect specific pathogens by identifying or detecting a body's reaction to such pathogens in addition to or instead of the pathogen itself Similarly or alternatively, the systems described herein may determine possible or likely infection by detecting chemical or biological materials (e.g., proteins) that may be related to infection by one or more pathogens.

The systems and methods described herein are also applicable to detection of environmental hazards such as ethylene, methylene, other volatile organic compounds (VOCs), and biological agents intended to cause harm to humans. Accordingly, the systems and methods allow for early detection and appropriate mitigation of such environmental hazards. In general, the systems and methods described herein may be utilized to detect any particle of interest that may pose a threat to human and/or animal health and/or harm the environment.

FIG. 1A depicts an example particle of interest detection environment 100 in some embodiments. The particle of interest detection environment 100 includes an apparatus 106A through an apparatus 106N, which may be or include food processing apparatuses, a spectral acquisition apparatus 102A through a spectral acquisition apparatus 102N, a computing device 110A through a computing device 110N, a communication network 108, and a particle of interest detection system 104. Although a single particle of interest detection system 104 is depicted in FIG. 1A, the particle of interest detection environment 100 may include any number of particle of interest detection systems 104. The particle of interest detection environment 100 may also include other systems, apparatuses, devices, machines, and/or components not illustrated in FIG. 1A, such as cleaning systems, water supply and water drain systems, and/or electrical and communication systems.

The apparatus 106 may be or include any device, machine, and/or apparatus that processes food or facilitates processing food for human or animal consumption. For example, the apparatus 106 may be a washing machine that washes fruits and vegetables such as leafy greens, apples, carrots, and the like using water. As another example, the apparatus 106 may be a commercial spinner that dries washed lettuce and other vegetables, which produces water to be drained away. Other examples of apparatuses 106 are within the scope of this disclosure. The apparatus 106 may be or include any number of digital devices. Digital devices are discussed, for example, with reference to FIG. 16. The apparatus 106 may be connected to the communication network 108.

The spectral acquisition apparatus 102 may be utilized as a part of a method to detect particles of interest. Particles of interest may be pathogens that affect the environment and/or human health and/or safety. For example, the particles of interest may include metals such as lead, arsenic, or mercury, toxins produced by bacteria such as coliform bacteria that may be found in water, air, or other bodily fluid such as blood or urine. The spectral acquisition apparatus 102 may be or include any number of digital devices. The spectral acquisition apparatus 102 may be or include any spectral acquisition device, but not limited to spectrometer, spectrophotometers, thermal emissions spectrometer, or other electromagnetic sources and detectors. A spectral acquisition device may be any device capable of obtaining spectral metrics and/or spectral data from the electromagnetic spectrum to find particles of interest, which may be invisible to unaided humans. In one example, the spectral acquisition apparatus 102 may be a Hach DR3900 spectrophotometer of the Hach Company of Loveland, Colorado, United States of America. In some embodiments, the spectral acquisition apparatus 102 may be a spectrometer of the INSION GmbH company of Germany. In another example, the spectral acquisition apparatus 102 may each be or include a different spectrophotometer, spectrometer, sensor, or detector capable of network communication. The spectral acquisition apparatus 102 may perform the functions of a spectrophotometer or a spectrometer. The spectral acquisition apparatus 102 may receive samples of food processing byproducts, detect light that has passed through the samples, and measure intensities of a set of wavelengths of the electromagnetic spectrum or light that has passed through the samples. The spectral acquisition apparatus 102 may then transmit a set of spectral metrics based on the measured intensities for the set of wavelengths of the electromagnetic spectrum or electromagnetic energy to the computing device 110. The set of spectral metrics may be the measured intensities, or they may be other values based on the measured intensities, such as absorbance, transmittance, reflectance, and/or scattering values.

The computing device 110 may be or include any number of digital devices. A software application 112 (not illustrated in FIG. 1A) may be executed by the computing device 110. The software application 112 may receive the set of spectral metrics which the spectral acquisition apparatus 102 obtains based on interactions of electromagnetic radiation with the samples, such as samples of food processing byproducts. In some embodiments, the software application 112 processes multiple sets of spectral metrics received from the spectral acquisition apparatus 102 as the software application 112 receives it. In one example, the software application 112 processes multiple sets of spectral metrics after the software application 112 receives all of them.

In one example, the computing device 110 may be a laptop and may be connected to the spectral acquisition apparatus 102 via a physical cable, such as a Universal Serial Bus (USB) cable. In some embodiments, the spectral acquisition apparatus 102 and the computing device 110 are not directly connected via a physical cable but are indirectly connected through a network, such as an IP-based Local Area Network (LAN), which may be part of or connected to the communication network 108. The software application 112 may perform processing steps before transmitting the processed data to the particle of interest detection system 104.

The particle of interest detection system 104 may be or include any number of digital devices. The particle of interest detection system 104 may receive the set of spectral metrics, process the set of spectral metrics as described herein, generate a particle of interest detection notification, and provide the particle of interest detection notification. In one example, the particle of interest detection system 104 utilizes machine learning (ML) and/or artificial intelligence (AI) models to detect evidence of particles of interest based on the set of spectral metrics. The ML and/or AI technology enables significantly reduced limits of detection (LOD), well beyond the LOD of the spectrophotometer (or other spectral acquisition device) alone. LOD is classically limited by the capabilities of the hardware and optical components. ML and/or AI reaches beyond hardware and optical limitations.

In various embodiments, the particle of interest detection system 104 may be a cloud-based application. In one example, the particle of interest detection system 104 may include serverless computing in which a cloud provider assigns computing resources on-demand. In some embodiments, the particle of interest detection system 104 provides the particle of interest detection notification to the computing device 110.

The spectral acquisition apparatus 102, the computing device 110, and/or the particle of interest detection system 104 may, in the event of a positive particle of interest detection notification, notify third-party systems such as those operated by food processors, those operated by government agencies such as the U.S. FDA, and/or those operated by third parties approved by such government agencies. In such an event, the spectral acquisition apparatus 102, the computing device 110, and/or the particle of interest detection system 104 may also recommend further diagnostic analysis by government agencies or other third parties approved by the government agencies.

In some embodiments, communication network 108 represents one or more computer networks (for example, LANs, WANs, and/or the like). The communication network 108 may provide communication between any of the apparatuses 106, any of the spectral acquisition apparatuses 102, any of the computing devices 110, and the particle of interest detection system 104. In some implementations, the communication network 108 comprises computer devices, routers, cables, and/or other network topologies. In some embodiments, the communication network 108 may be wired and/or wireless. In various embodiments, the communication network 108 may comprise the Internet, one or more networks that may be public, private, IP-based, non-IP based, and so forth.

Some embodiments described herein discuss performing spectral analysis on water samples (e.g., obtained from wash water), such as those obtained directly or indirectly from apparatuses 106. It will be appreciated that the spectral acquisition apparatus 102, the computing device 110, and/or the particle of interest detection system 104 may perform spectral analysis on any sample, such as samples of food processing byproducts. Examples of food processing byproducts include, but are not limited to, water, wash water, oils, greases, animal blood, meat, and feces from animals such as cows, pigs, and chickens. Furthermore, samples may be obtained by swabbing or otherwise sampling food processing equipment, surfaces, residues, or anything that comes into contact with food. It will be understood that food processing byproducts are not limited to the examples described herein.

Figure 1B:
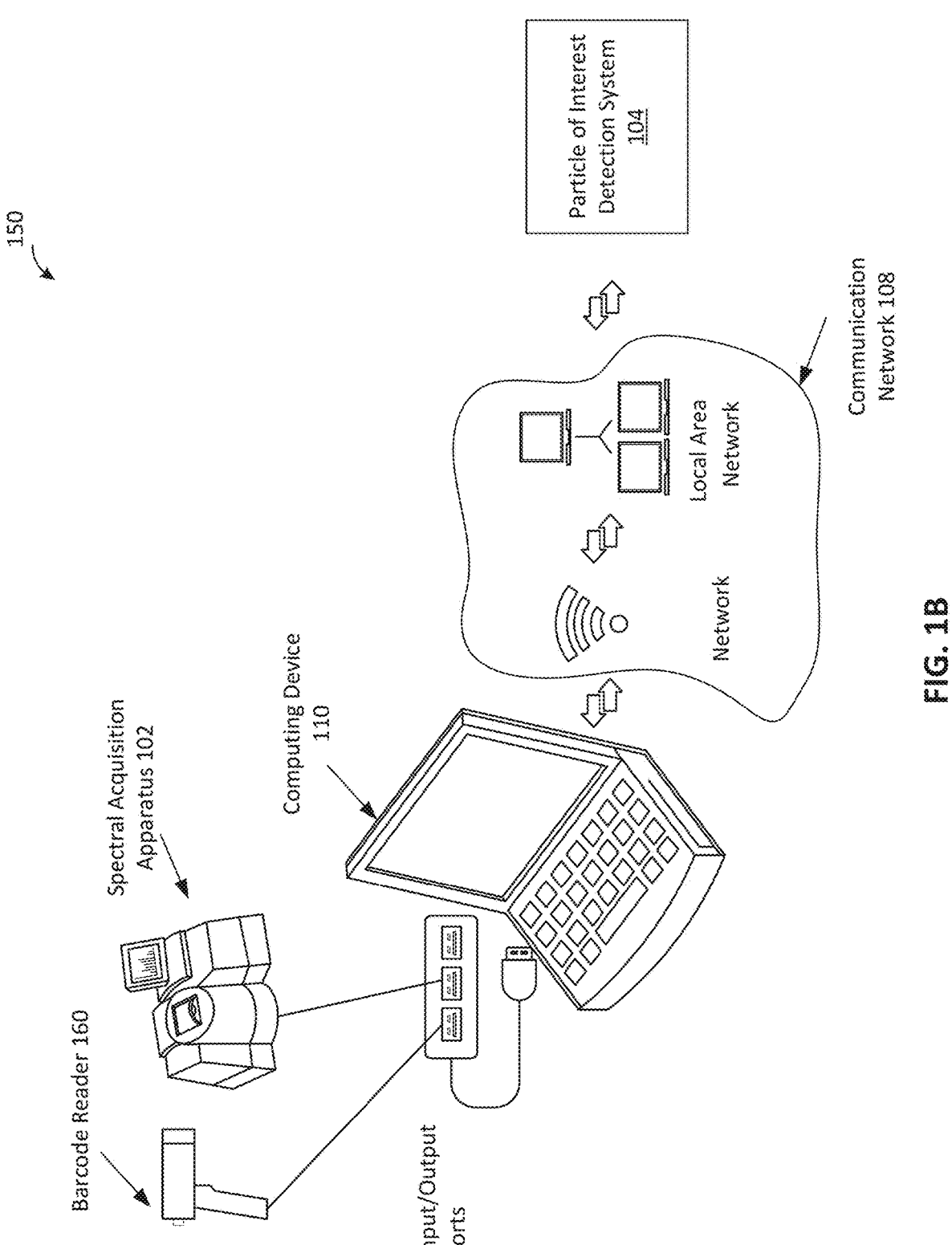
FIG. 1B depicts another example particle of interest detection environment according to some embodiments.

FIG. 1B depicts another example of particle of interest detection environment 150 according to some embodiments.

In the illustrated embodiment of particle of interest detection environment 150, the spectral acquisition apparatus 102 is a spectrophotometer. A sample of food processing byproducts may be obtained and placed in a container such as a cuvette or test tube. The cuvette may include a machine-readable code such as a barcode or a quick-response (QR) code. The particle of interest detection environment 150 may include a barcode reader 160 or an image capture device coupled to a mobile computing device. The barcode reader may be coupled to the computing device 110 via a cable, such as a USB cable.

The computing device 110 may receive data from a plurality of spectral acquisition apparatuses. The output of each spectral acquisition apparatus may be in different file formats. For example, the output of one spectral acquisition apparatus may be in a comma-separated values (CSV) file format, while the output of another spectral acquisition apparatus may be in an extensible markup language (XML) file format. Furthermore, the format of the data may vary depending on a manufacturer and/or model of the spectral acquisition apparatus.

Figure 2A:
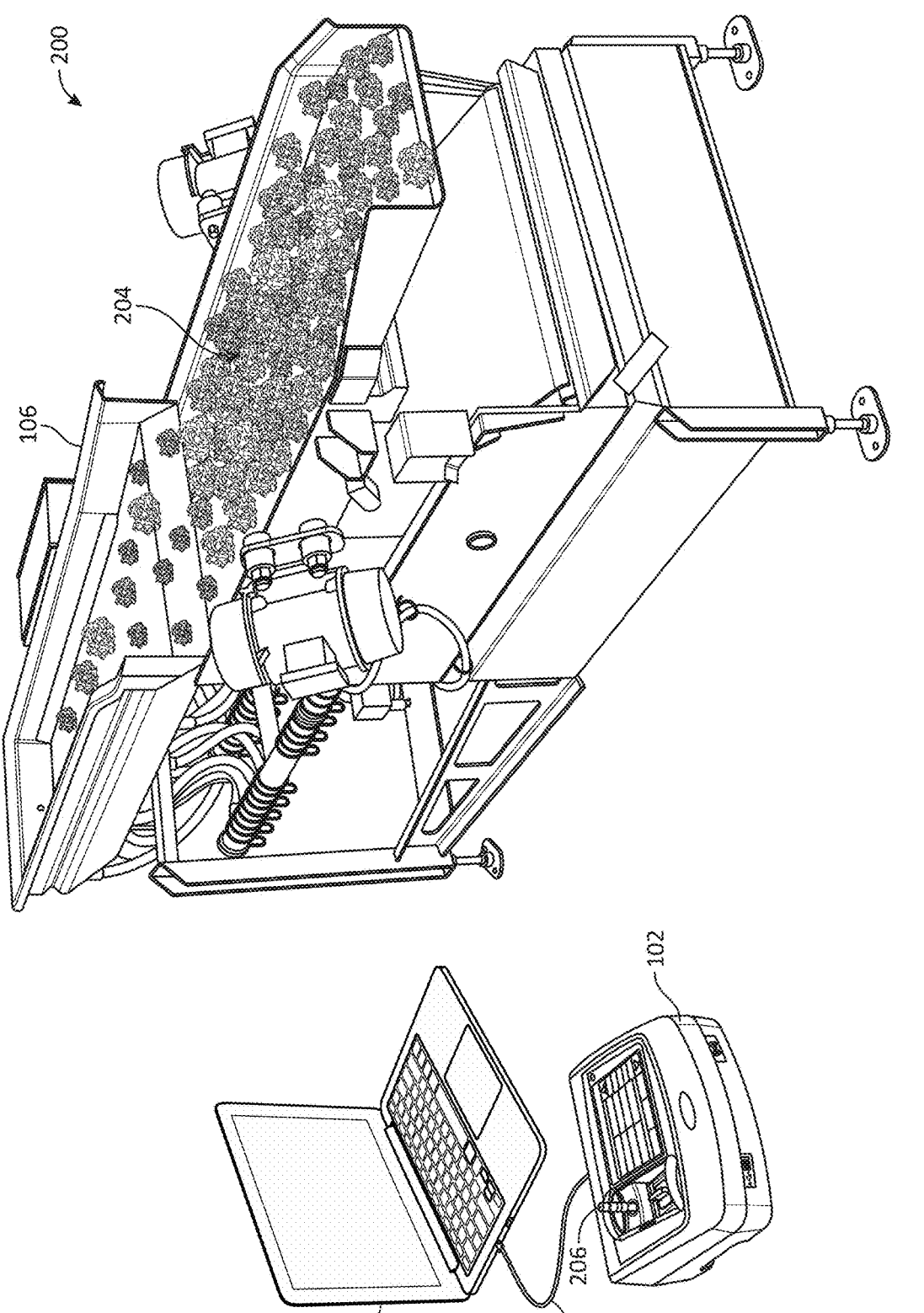
FIG. 2A depicts an example food processing apparatus, an example computing device, and an example spectral acquisition apparatus in some embodiments.

FIG. 2A depicts an example food processing environment 200 in some embodiments. The food processing environment 200 includes the apparatus 106, which is a food processing apparatus, the spectral acquisition apparatus 102, and a computing device 110 connected to the spectral acquisition apparatus 102 via a cable 202, which may be a Universal Serial Bus (USB) cable. The apparatus 106 has pieces of produce 204, such as lettuce, on it to be washed. The spectral acquisition apparatus 102 and the computing device 110 may be positioned proximate to the apparatus 106 and may be positioned on a support (e.g., a bench, a table, or the like, not illustrated in FIG. 2A).

The spectral acquisition apparatus 102 may perform scans of samples of food processing byproducts and obtain spectral metrics based on light that has passed through the samples. The samples may be placed in a cuvette 206 positioned in a receptacle of the spectral acquisition apparatus 102. For example, the spectral acquisition apparatus 102 may obtain a set of intensity measurements of a set of wavelengths of the light that has passed through the sample. The spectral acquisition apparatus 102 may convert the intensity measurements in the set of intensity measurements to other values, such as absorbance values, transmittance values, reflection values, scattered values or concentration values. The spectral acquisition apparatus 102 may transmit data including the spectral metrics in a first format to the computing device 110. In some embodiments, the spectral acquisition apparatus 102 transmits the set of intensity measurements to the computing device 110. In some embodiments, the spectral acquisition apparatus 102 measures the detected light in units other than intensity, such as in absorbance units or transmittance units, and transmits the measured other values to the computing device 110. In some embodiments, the spectral acquisition apparatus 102 transmits the spectral metrics to the particle of interest detection system 104. In some embodiments, the spectral acquisition apparatus 102 transmits the spectral metrics to both the computing device 110 and to the particle of interest detection system 104.

Figure 2B:
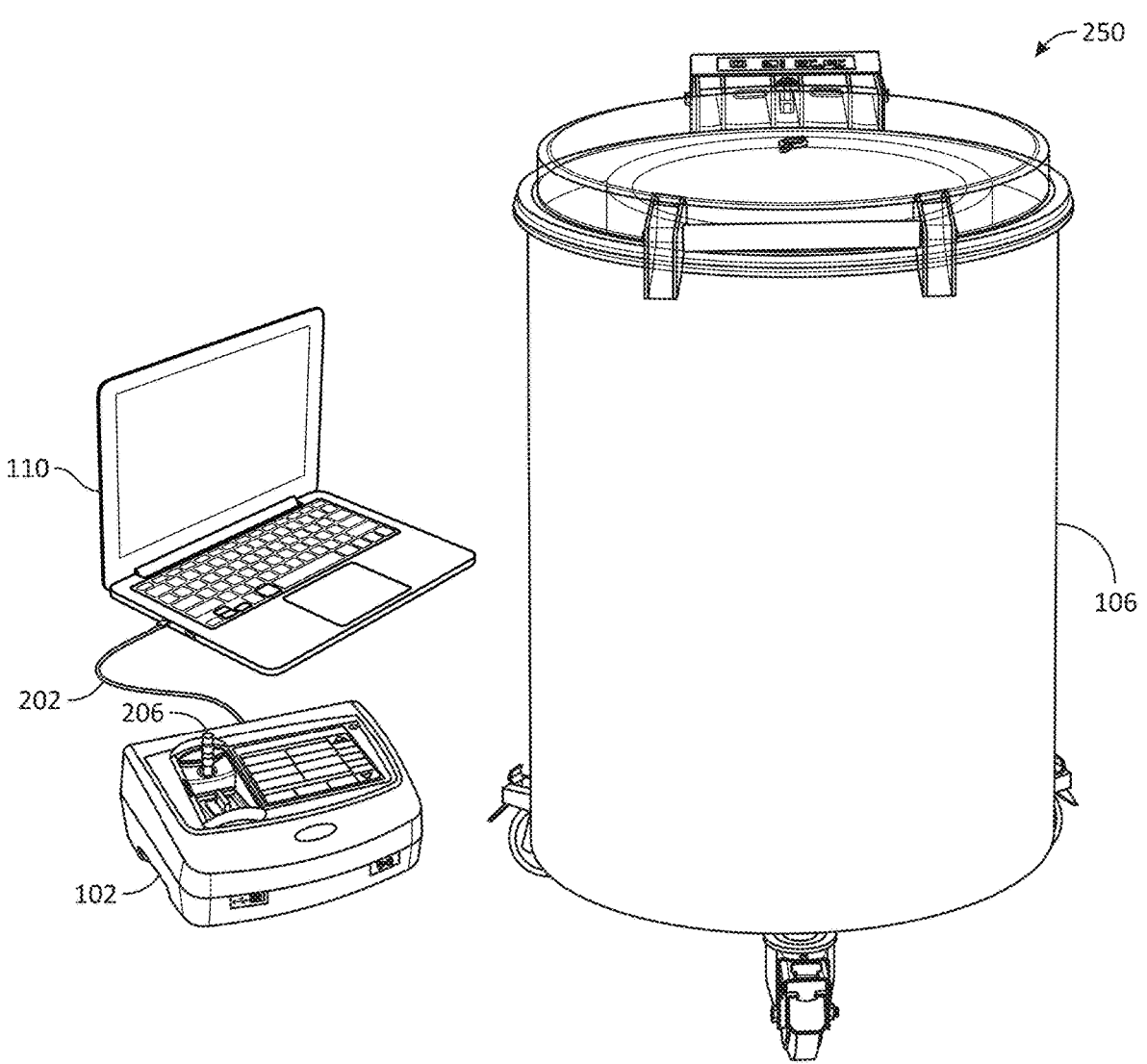
FIG. 2B depicts another example food processing apparatus, an example computing device, and an example spectral acquisition apparatus in some embodiments.

FIG. 2B depicts another example food processing environment 250 in some embodiments. In the food processing environment 250, the apparatus 106 is a salad spinner that may be used to dry wet lettuce or other wet produce. The apparatus 106 produces water as it spins, which may drain via one or more drain lines (not illustrated in FIG. 2B). Other like reference numerals in FIG. 2B refer to like elements in FIG. 2A and are not discussed with reference to FIG. 2B.

Figure 3A:
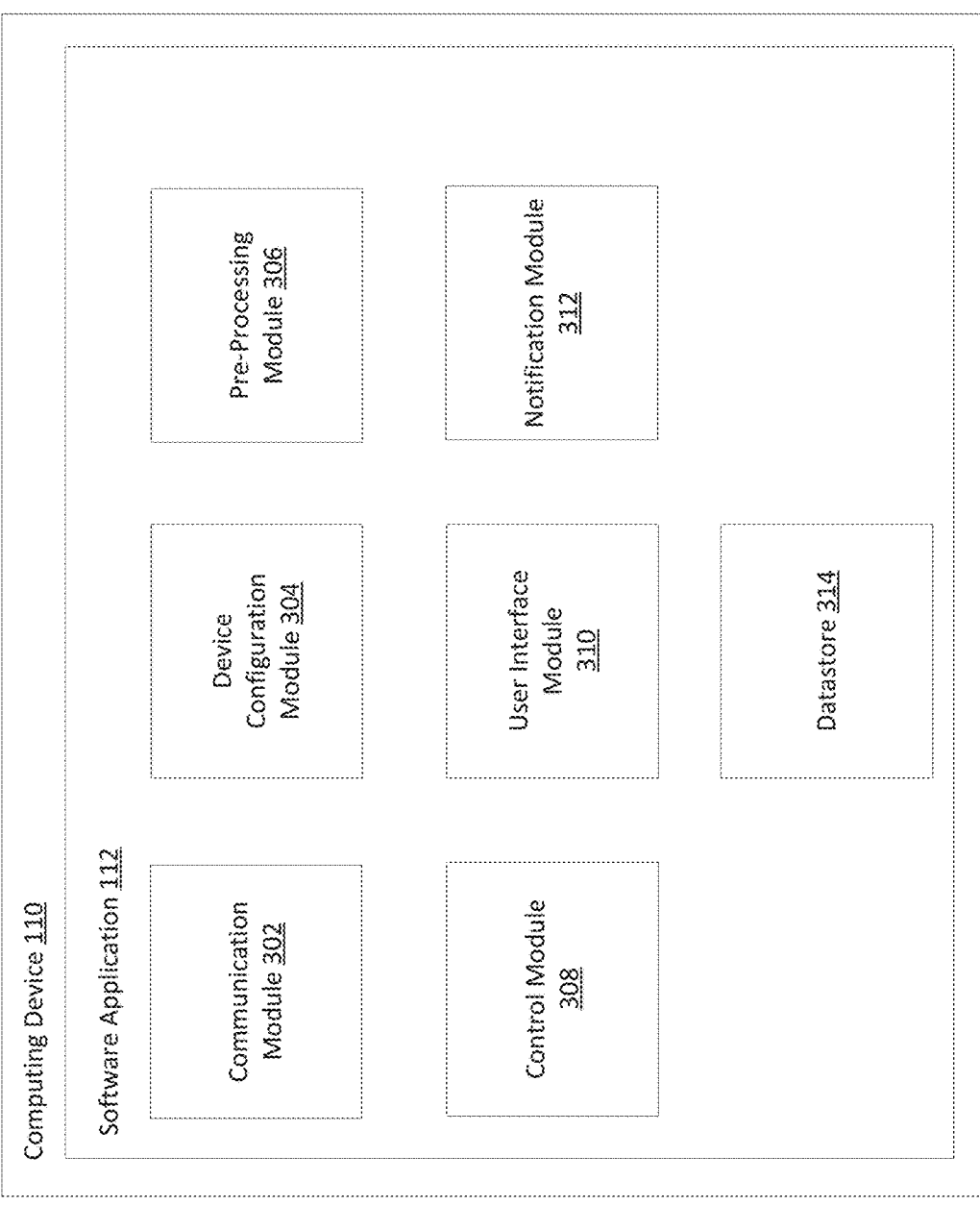
FIG. 3A is a block diagram of components of an example computing device in some embodiments.

FIG. 3A is a block diagram of components of a computing device 110 in some embodiments. The computing device 110 includes the software application 112. The software application 112 includes a communication module 302, a device configuration module 304, a pre-processing module 306, a control module 308, a user interface module 310, a notification module 312, and a datastore 314.

The communication module 302 may send and/or receive requests and/or data between the computing device 110 and any of the apparatuses 106, the particle of interest detection system 104, and the spectral acquisition apparatuses 102. The communication module 302 may receive requests and/or data from the apparatuses 106, the particle of interest detection system 104, and/or the spectral acquisition apparatuses 102. The communication module 302 may also send requests and/or data to the apparatuses 106, the particle of interest detection system 104, and/or the spectral acquisition apparatuses 102.

The device configuration module 304 may include an Application Programming Interface (API) or other interface to allow the spectral acquisition apparatus 102 to communicate with the computing device 110. In some embodiments, the device configuration module 304 may identify a manufacturer, type, or model of the spectral acquisition apparatus 102. Once the device configuration module 304 makes the identification, the software application 112 may identify properties or parameters of spectrometer data that may be sent by spectral acquisition apparatus 102. In one example, the device configuration module 304 determines that the spectral acquisition apparatus 102 is a Hach DR3900 spectrophotometer. Once the device configuration module 304 identifies the manufacturer, type, or model of the spectral acquisition apparatus, the device configuration module 304 may identify a precision or accuracy of the light intensity measurement, available file formats of the output of the spectral acquisition apparatus 102, and other properties associated with the spectral acquisition apparatus. These properties may include whether or software application 112 is able to control the spectral acquisition apparatus 102 or only able to read data from the spectral acquisition apparatus 102, name of the spectral acquisition apparatus 102, data bit depth, step size, integration time, firmware version, and serial number of the spectral acquisition apparatus 102.

The pre-processing module 306 may receive data from the spectral acquisition apparatus 102 in a first format. The pre-processing module 306 may receive from the device configuration module 304 information regarding the file format and the format of the data. In one example, the output of one spectral acquisition apparatus may be in the CSV file format, while the output of another spectral acquisition apparatus may be in an XML file format. The pre-processing module 306 may normalize or arrange the set of values received from the different spectral acquisition apparatuses of the particle of interest detection environment 100 so that it may be inputted into the artificial intelligence and/or machine learning system of the particle of interest detection system 104. The output of the pre-processing module 306 may be a second format, which may be stored in the datastore 314. The second format may include the spectral metrics.

In various embodiments, the file format of the output of one spectral acquisition apparatus is a different file format from another spectral acquisition apparatus. In some embodiments, the pre-processing module 306 may format the data according to the requirements of the artificial intelligence and/or machine learning system of the particle of interest detection system 104.

Certain models of spectral acquisition apparatuses 102 may allow the spectral acquisition apparatus 102 to be remotely controlled by a software application or a computing device. For example, certain models of spectral acquisition apparatuses 102 may include an Application Programming Interface (API) that allows a software application or a computing device to control the spectral acquisition apparatus 102 via the API. In one example, the API of the Hach DR3900 spectrophotometer may include instructions that allow the user of the computing device 110 to identify the number of spectral acquisition apparatuses remotely controllable by the computing device 110, open communication or connect to the spectral acquisition apparatuses 102, close communication or disconnect the spectral acquisition apparatuses 102, provide to the computing device 110 error messages associated with the spectral acquisition apparatuses 102, and read one or more sets of values from the spectral acquisition apparatuses 102.

Other models of spectral acquisition apparatus 102 may allow a software application or a computing device to only receive data from the spectral acquisition apparatus 102. In cases where the spectral acquisition apparatus 102 may be remotely controlled by the software application 112, the control module 308 of the software application 112 may control the spectral acquisition apparatus 102. In one example, the control module 308 may power up or start up the spectral acquisition apparatus 102. In some embodiments, the control module 308 may send a request to the spectral acquisition apparatus 102 to identify and scan a cuvette or test tube placed in the spectral acquisition apparatus 102.

In some embodiments, the control module 308 may send a request to the AI/ML of the particle of interest detection system 104 to detect evidence of particles of interest in the spectrometer scans. The AI/ML determines if the result of the detection indicates a positive particle of interest detection or a negative particle of interest detection. If the result meets or exceeds a threshold, then the AI/ML may output a positive particle of interest detection, and if the result does not meet or exceed a threshold, then the AI/ML may output a negative particle of interest detection. The particle of interest detection system 104 may send the result to the user interface module 310 of the software application 112.

Figure 16:
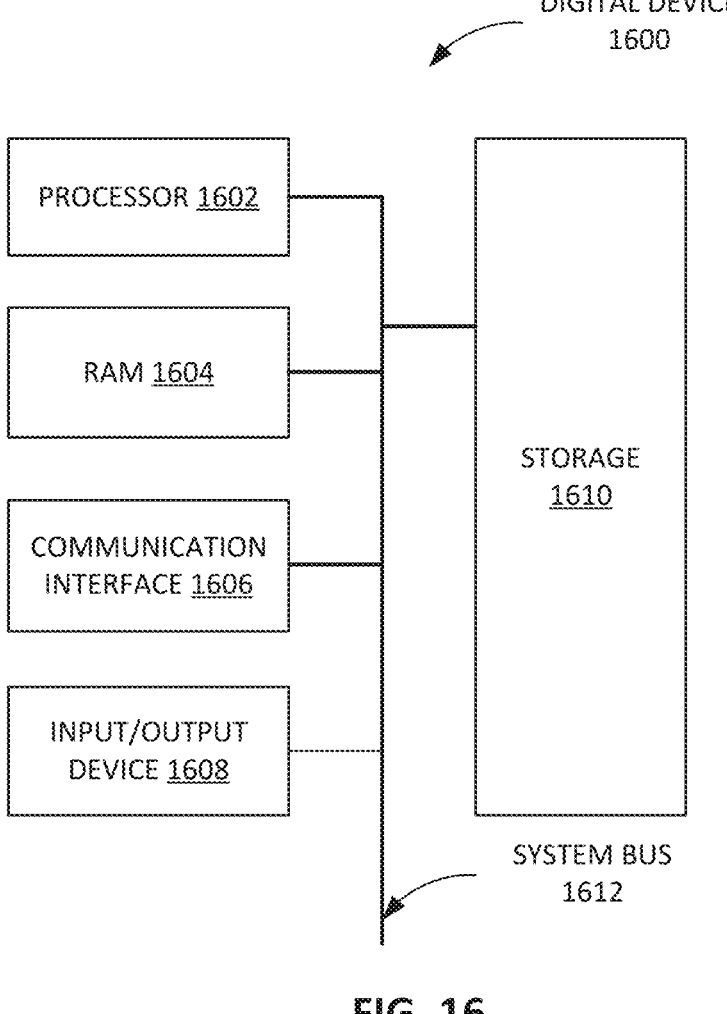
FIG. 16 depicts a block diagram of an example digital device in some embodiments.

The user interface module 310 may provide user interfaces to the input/output device 1608 of the digital device 1600 of FIG. 16. In some embodiments, the user interface module 310 provides a user interface that allows users to log in to securely access the software application 112. In one example, the user interface module 310 provides a notification to a user of the computing device 110 of the positive or negative particle of interest detection provided by the AI/ML of the particle of interest detection system 104 in the form of a pop-up window of the user interface.

In some embodiments, the user interface module 310 may provide multiple particle of interest test results to the user interface.

In some embodiments, the type of notification provided to the user by the notification module 312 may depend on the type of pathogen being tested or concentration of the pathogen. The notification module 312 may provide a pop-up window to the user interface provided by the user interface module 310. In some embodiments, the notification module 312 may send an email to the user of the software application 112, who may be a lab technician who prepared and tested the sample of water, a text message, a short message/messaging service (SMS), or a telephone call.

The notification module 312 may provide reports, alerts, and/or dashboards that include results, confidence scores, and/or other information.

For example, the computing device 110 may receive the results of particle of interest detections on particular food processing equipment as well as what food was processed on the food processing equipment. As another example, the computing device 110 may receive the results of particle of interest detections in certain parts of a food processing facility as well as what food was processed in those certain parts. The computing device 110 may thus be able to identify food (e.g., particular lots or production runs) and recommend, via the notification module 312, that remedial action, such as quarantining food, recalling food, or other action, should be taken. The notification module 312 may optionally notify appropriate third parties (e.g., government agencies such as the U.S. FDA) of the detection of foodborne pathogens. The notification module 312 may, in some embodiments, prepare reports to aid in compliance with food safety laws and regulations.

The datastore 314 may include data stored, accessed, and/or modified by any of the modules of the computing device 110. The datastore 314 may include any number of data storage structures such as tables, databases, lists, and/or the like.

Although the software application 112 is depicted as described as including modules 302 through 312 and notification module 312, the modules and/or datastore may be included in the computing device 110. One or more modules and/or datastore of the software application 112 as seen in FIG. 3A may be included in the computing device 110.

Figure 3B:
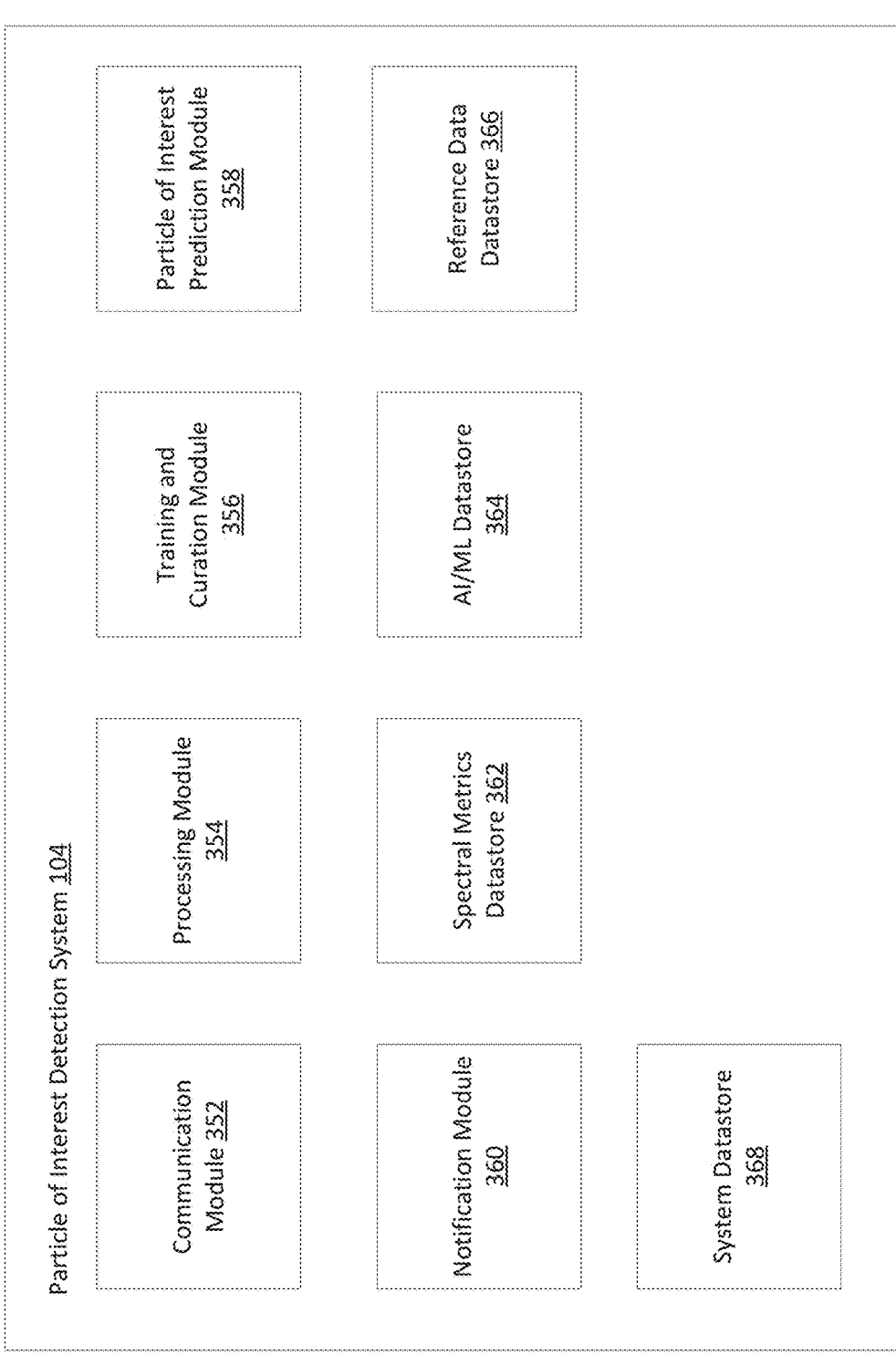
FIG. 3B is a block diagram of components of an example particle of interest detection system in some embodiments.

FIG. 3B is a block diagram of components of the particle of interest detection system 104 in some embodiments. The particle of interest detection system 104 includes a communication module 352, a processing module 354, a training and curation module 356, a particle of interest prediction module 358, a notification module 360, a spectral metrics datastore 362, an AI/ML datastore 364, a reference data datastore 366, and a system datastore 368.

The communication module 352 may send and/or receive requests and/or data between the particle of interest detection system 104 and any of the apparatuses 106, the computing devices 110, and the spectral acquisition apparatuses 102. The communication module 352 may receive requests and/or data from the apparatuses 106, the computing devices 110, and/or the spectral acquisition apparatuses 102. The communication module 352 may also send requests and/or data to the apparatuses 106, the computing devices 110, and/or the spectral acquisition apparatuses 102.

The processing module 354 may receive a request from the software application 112 that data from the spectral acquisition apparatus 102 will be transmitted to the processing module 354. The processing module 354 may receive this request and transmit a request to the particle of interest prediction module 358 that data will be transmitted to the particle of interest prediction module 358. In some embodiments, the data transmitted to the processing module 354 may be a first set of data in the first format. In one example, the data transmitted to the processing module 354 may be a second set of data in the second format. The first set of data in the first format may be processed to obtain the second set of data in the second format.

The training and curation module 356 may train an artificial intelligence and/or machine learning system (e.g., such as a set of decision trees) to be applied to the processed data from the spectral acquisition apparatus 102.

The particle of interest prediction module 358 may apply the trained artificial intelligence and/or machine learning system (e.g., such as the set of trained decision trees) to the set of spectral metrics received from the computing device 110 or a set of values based on the set of spectral metrics to obtain a result. The artificial intelligence and/or machine learning system may have been previously trained by the training and curation module 356. In some embodiments, the particle of interest prediction module 358 may be previously trained to detect particles of interest. Particles of interest may be pathogens that affect the environment or human health and safety. In one example, a result may indicate either a positive (a positive particular of interest detection) or a negative (a negative particular of interest detection) for a foodborne pathogen for the sample of the food processing byproduct.

The machine learning and/or artificial intelligence technology enables significantly reduced limits of detection (LOD), well beyond the LOD of the spectrophotometer (or other spectral acquisition device) alone. LOD is classically limited by the capabilities of the hardware and optical components. Machine learning and/or artificial intelligence technology reaches beyond hardware and optical limitations.

The notification module 360 may generate and provide notifications that include results of particle of interest detections for the sample as well as other information, such as a confidence score. The notification module 360 may provide reports, alerts, and/or dashboards that include results, confidence scores, and/or other information. For example, the particle of interest detection system 104 may track foodborne pathogen detections on particular food processing equipment as well as what food was processed on the food processing equipment. As another example, the particle of interest detection system 104 may track foodborne pathogen detections in certain parts of a food processing facility as well as what food was processed in those certain parts. The particle of interest detection system 104 may thus be able to identify food (e.g., particular lots or production runs) and recommend, via the notification module 360, that remedial action, such as quarantining food, recalling food, or other action, should be taken. The notification module 360 may optionally notify appropriate third parties (e.g., government agencies such as the U.S. FDA) of the detection of foodborne pathogens. The notification module 360 may, in some embodiments, prepare reports to aid in compliance with food safety laws and regulations.

The spectral metrics datastore 362 stores raw data received from the spectral acquisition apparatus 102. A data store is any data structure (e.g., one or more tables, databases, and/or the like) for storing information. The raw data may be stored for auditing purposes. In some embodiments, the spectral metrics datastore 362 receives pre-processed data from the pre-processing module 306 of FIG. 3A. The spectral metrics datastore 362 may include any number of data storage structures such as tables, databases, lists, and/or the like.

The AI/ML datastore 364 stores artificial intelligence/machine learning models (e.g., such as a set of decision trees) used to detect evidence of foodborne pathogens in the spectrometer scans. In some embodiments, the AI/ML datastore 364 stores the results of the artificial intelligence/machine learning models. In some embodiments, the artificial intelligence/machine learning models are stored on the particle of interest detection system 104, which may be a cloud-based application. In various embodiments, the artificial intelligence/machine learning models are stored locally on the same network as the apparatus 106. In one example, the artificial intelligence/machine learning models are stored on edge devices. An edge device is a device that provides an opening or entry point into an enterprise network. For security reasons, some corporations may require the artificial intelligence/machine learning models to be stored locally instead of storing the artificial intelligence/machine learning model in a cloud-based application that may be external to the corporation's enterprise network.

The reference data datastore 366 stores reference data and metadata associated with the spectrometer data, spectrometer, and properties associated with the data.

For example, reference data may include the name of the manufacturer, model, and the serial number of the spectral acquisition apparatus, operator identifier (ID), and spectral acquisition apparatus firmware version.

In one example, metadata may include a scan universal unique identifier, an external reference identifier, a specimen scanned data timestamp, which may be the date and time at which the spectral acquisition apparatus obtains the set of spectral metrics, spectral data file name, target particle or pathogen, inference request type name, operator ID, scan mode type code or name, medium name, modality name, device model, scan code or version code, device ID, location code name, customer ID, software version number code, and device firmware version identifier.

The scan universal unique identifier may be an identifier or identification number associated with a particular sample or specimen.

The external reference identifier may be a unique identifier for a particular sample assigned by a customer. The external reference identifier may link to a particular data file and metadata associated with the particular sample. The external reference identifier may enable a chain of custody which may be used for tracking purposes.

The specimen scanned data timestamp may include a date and timestamp of when the sample or specimen was scanned by the computing device 110.

The spectral data file name may be the name of the spectral data file.

The target particle or pathogen may be a name of the pathogen or particle that the particle of interest detection system 104 is trying to detect. In some embodiments, the target particle or pathogen may be *E. Coli, Salmonella,* or *Listeria,* or a pathogen that infects humans such as Respiratory Syncytial Virus (RSV), or Coronavirus (COVID-19).

The inference request type name specifies whether the result or inference needs to be sent to the software application 112 or not. The metadata associated with the inference request type name may be synchronous or asynchronous. A synchronous value may represent that the result of the data acquired and processed by the particle of interest detection system 104 may be communicated or sent to the software application 112. An asynchronous value may represent that the result of the data acquired and processed by the particle of interest detection system 104 may not be communicated or sent to the software application 112.

In one example, the operator ID may be an internal ID number or name associated with a particular user of the 110 or laboratory technician.

Metadata associated with the scan mode type code or name may specify whether the sample or specimen was scanned in transmission mode or absorbance mode. The results of scans in transmission mode may be expressed as a percentage or ratio (% T). The results of scans in absorbance mode may be expressed in Absorbance Unit (AU). In one example, for Hach spectrophotometers, to convert from Absorbance Unit to transmission ratio, the following equation may be utilized:

$$\% \ T = \text{antilog}(2 - AU)$$

In various embodiments, the medium name identifies the medium in which the target particle is prepared for a scan. Examples of medium names may include DI Water, phosphate buffer solution (PBS), saline water, CITOSWAB®.

In another example, the modality name may refer to where the target particle was collected from. Examples of modality names include low nasal swabs, upper nasal swabs, oral swabs, oral rinse, urine, and blood sample.

The device mode may refer to whether the spectral metrics is processed by the artificial intelligence and/or machine learning system right away or if the spectral metrics is not processed right away.

In some embodiments, the scan code or version code may be a code that is generated by the particle of interest detection system 104 when the particle of interest detection system 104 is in operation mode (e.g., non-training mode). The scan code or version code may be used to validate user input.

The device ID may be an identifier assigned by the software application.

In one example, the location code name may represent an identifier of where a particular piece of equipment or device is deployed for sample/specimen collection.

In some embodiments, the customer ID is an identifier for each customer of the particle of interest detection system 104.

The software version number code and device firmware version identifier may represent or identify the version of the software being used.

The system datastore 368 stores the results of foodborne pathogen detections of the sample as well as other information, such as a confidence score. Reports and/or dashboards that include results, confidence scores, and/or other information may be stored in the system datastore 368.

A module of the computing device 110 or the particle of interest detection system 104 may be hardware, software, firmware, or any combination. For example, each module may include functions performed by dedicated hardware (e.g., an Application-Specific Integrated Circuit (ASIC), a Field Programmable Gate Array (FPGA), or the like), software, instructions maintained in ROM, and/or any combination. Software may be executed by one or more processors. Although a limited number of modules are depicted in FIGS. 3A and 3B, there may be any number of modules. Further, individual modules may perform any number of functions, including functions of multiple modules, as shown herein. Further, modules depicted as being included in the computing device 110 may be additionally or alternatively included in the particle of interest detection system 104, and modules included in the particle of interest detection system 104 may be additionally or alternatively included in the computing device 110.

Figure 4:
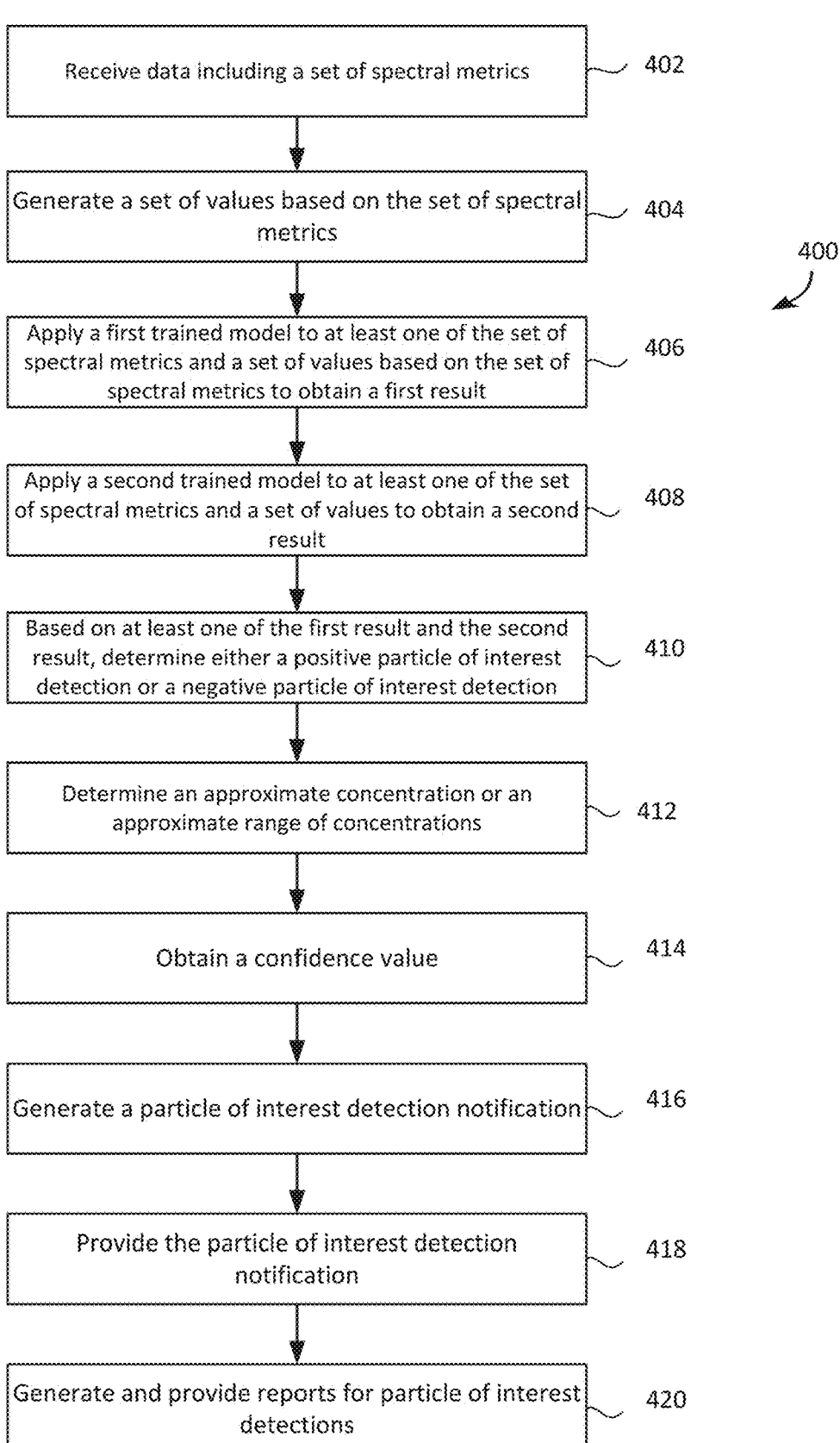
FIG. 4 is a flowchart showing a method for detecting particles of interest in some embodiments.

FIG. 4 is a flowchart showing a method 400 for detecting particles of interest in some embodiments. Various modules of both the computing device 110 and the particle of interest detection system 104 may perform the method 400. In some embodiments, various modules of only the computing device 110 perform the method 400. In some embodiments, various modules of only the particle of interest detection system 104 perform the method 400.

As discussed herein, the particle of interest detection system 104 may be employed to detect foodborne pathogens. The following may describe detection of foodborne pathogens, but it will be appreciated that the particle of interest detection system 104 may be utilized to detect any particle of interest.

In some embodiments, a person working in a food processing facility in which the apparatus 106 is located fills the cuvette 206 or other suitable container with a sample of food processing byproduct and places the cuvette 206 in an appropriate receptacle of the spectral acquisition apparatus 102. The person may fill the cuvette 206 periodically, as needed, for each lot or shipment of food to be processed, or on a predetermined schedule. It will be understood that samples of food processing byproducts may be tested at various times. In some embodiments, the cuvette 206 may be filled by an automated device or system without intervention by a person. In some embodiments, the sample of food processing byproduct may be mixed with a reagent and/or cultivated in a solution, such as a tryptic soy broth (TSB) solution. In some embodiments, the sample of food processing byproduct may be mixed with a neutral or inert substance.

After filling the cuvette 206, the person may then start a scan of the sample of the food processing byproduct using an interface of the spectral acquisition apparatus 102. Additionally, or alternatively, the person may start the scan using the computing device 110, which may control the spectral acquisition apparatus 102. The spectral acquisition apparatus 102 may generate electromagnetic radiation that interacts with the sample. For example, the spectral acquisition apparatus 102 may generate light that passes through at least a portion of the sample of the food processing byproduct in the cuvette 206 and detect the light that has passed through at least the portion of the sample of the food processing byproduct in the cuvette 206. The spectral acquisition apparatus 102 may measure the intensities of the detected light for a set of wavelengths of the light and obtain a set of intensity measurements for the set of wavelengths of the light. The spectral acquisition apparatus 102 may convert the intensity measurements in the set of intensity measurements to other values, such as absorbance values, transmittance values, reflection values, scattered values or concentration values.

In some embodiments, the set of wavelengths of light includes wavelengths of light in the ultraviolet, visible, and infrared spectrums. In some embodiments, the set of wavelengths of light includes wavelengths of light ranging from approximately 300 nanometers (nm) (for example, approximately 320 nm) to approximately 1100 nm (for example, approximately 1100 nm). In some embodiments, the spectral acquisition apparatus 102 has a resolution of 1 nm and obtains a set of 781 intensity measurements for a set of 781 wavelengths of light. The spectral acquisition apparatus 102 obtains a set of spectral metrics based on interactions of the electromagnetic radiation with the sample.

Additionally or alternatively, the spectral acquisition apparatus 102 may measure absorbance, transmittance, reflectance and/or scattering of electromagnetic radiation to obtain the set of spectral metrics. The electromagnetic radiation generated by the spectral acquisition apparatus 102 may include ultraviolet light, visible light, and/or infrared light. The spectral acquisition apparatus 102 may also utilize electromagnetic radiation from portions of the electromagnetic spectrum other than ultraviolet, visible, and infrared portions.

The method 400 may begin at step 402, where the communication module 352 receives a first set of data from the spectral acquisition apparatus 102. The first set of data includes the set of spectral metrics. The set of spectral metrics may be or be based on a set of intensity measurements for a set of wavelengths of light that the spectral acquisition apparatus 102 obtained. Additionally or alternatively, the set of spectral metrics may be or be based on absorbance, transmittance, reflectance and/or scattering measurements that the spectral acquisition apparatus 102 obtains.

In some embodiments, the set of spectral metrics from the spectral acquisition apparatus 102 may be stored in the spectral metrics datastore 362 of the particle of interest detection system 104. A copy of data from the spectral acquisition apparatus 102 may be stored in the particle of interest detection system 104 for various purposes, such as for auditing purposes.

At step 404, the processing module 354 generates a set of values based on the set of spectral metrics. In some embodiments, the processing module 354 normalizes each value in the set of values to be between zero, inclusive, and one, inclusive. The processing module 354 may further process the values in the set of values. For example, the processing module 354 may apply a fitting function to each normalized value in the set of values. In some embodiments, the processing module 354 applies a smoothing filter, such as a Savitzky-Golay filter utilizing a second-order polynomial, to the normalized values. In some embodiments, the Savitzky-Golay filter utilizes a window having a size of 151. The processing module 354 may apply a Savitzky-Golay filter utilizing polynomials of other orders and/or of other window sizes. In some embodiments, the processing module 354 applies a rolling average to the set of values utilizing a window size of 10 and a slide value of 1. The processing module 354 may apply a rolling average utilizing other windows of other sizes and/or other slide values. In some embodiments, the processing module 354 applies other fitting functions and/or signal processing techniques to smooth out the values in the set of values and/or reduce noise in the values in the set of values.

At step 406, the particle of interest prediction module 358 applies one or more first trained machine learning or artificial intelligence models to the set of spectral metrics or a set of values based on the set of spectral metrics received from the pre-processing module 306 to obtain a first result. The training and curation module 356 may have trained the one or more first machine learning or artificial intelligence models on a first set of training samples for first particles of interest and a second set of training samples for second particles of interest. The first particles of interest may include at least a first type of the first particles of interest and a second type of the first particles of interest. For example, the training and curation module 356 may have trained the one or more first machine learning or artificial intelligence models on a first set of training samples containing *Listeria*, such as *Listeria mono, Listeria innocua*, or both *Listeria mono* and *Listeria innocua*, and on a second set of training samples containing another particle of interest, such as *Escherichia coli* (*E. coli*), *Staphylococcus aureus*, or any of the types of *E. coli* or *Staphylococcus aureus*.

In some embodiments, the first set of training samples includes a first subset of training samples containing the first particles of interest at a first concentration and a second subset of training samples containing the first particles of interest at a second concentration different from the first concentration, and the second set of training samples includes a third subset of training samples containing the second particles of interest at a third concentration and a fourth subset of training samples containing the second particles of interest at a fourth concentration different from the third concentration.

In some embodiments, the particle of interest prediction module 358 applies a first set of trained decision trees to the set of spectral metrics or a set of values based on the set of spectral metrics received from the pre-processing module 306. In some embodiments, the particle of interest prediction module 358 utilizes the following Python code to apply the first set of trained decision trees to the set of values to obtain a result:

y_pred=model·predict(x_test)

In this code, y_pred is the result and x_test is testing data. In some embodiments, the first set of trained decision trees may operate in a binary mode. In such embodiments, the result may be a float that has a value between zero, inclusive, and one, inclusive. In some embodiments, the first set of trained decision trees may operate in a multiclass mode. In such embodiments, the result may be an integer that has value of either zero, one, or another integer value greater than one.

At step 408, the particle of interest prediction module 358 applies one or more second trained machine learning or artificial intelligence models to the set of spectral metrics or a set of values based on the set of spectral metrics received from the pre-processing module 306 to obtain a second result. The training and curation module 356 may have trained the one or more second machine learning or artificial intelligence models on a third set of training samples for the first type of the first particles of interest and a fourth set of training samples for the second type of the first particles of interest. For example, where the first particles of interest are *Listeria*, the training and curation module 356 may have trained the one or more second machine learning or artificial intelligence models on a third set of training samples for *Listeria mono* and a fourth set of training samples for *Listeria*.

In some embodiments, the third set of training samples includes a third subset of training samples containing the first type of the first particles of interest at a first concentration and a fourth subset of training samples containing the second type of the first particles of interest at a second concentration different from the first concentration. In some embodiments, the fourth set of training samples includes a third subset of training samples containing the second particles of interest at a third concentration and a fourth subset of training samples containing the second particles of interest at a fourth concentration different from the third concentration.

At step 410, the particle of interest prediction module 358, based on at least one of the first result and the second result, determines either a positive particle of interest detection or a negative particle of interest detection for the particle of interest in the sample of the food processing byproduct. In some embodiments, the particle of interest prediction module 358 determines that at least one of the first result and the second result indicates a positive particle of interest detection if at least one of the first result and the second result meets or exceeds a threshold, and that at least one of the first result and the second result indicates a negative particle of interest detection if at least one of the first result and the second result does not meet or exceed the threshold. In embodiments where at least one of the first result and the second result is a float value between zero, inclusive, and one, inclusive, the threshold may be 0.5. In embodiments where at least one of the first result and the second result is an integer with a value of either zero, one, or another integer value greater than one, zero indicates a negative particle of interest detection, and one or another integer value greater than one indicates a positive particle of interest detection. As discussed in more detail herein, in such embodiments, at least one of the first result and the second result may indicate both a positive particle of interest detection as well as a concentration of the particle of interest in the sample.

At step 412, the particle of interest prediction module 358, based on at least one of the first result and the second result, determines an approximate concentration or an approximate range of concentrations for at least one of the first particles of interest, the first type of the first particles of interest, and the second type of the first particles of interest in the sample. For example, the particle of interest prediction module 358 may determine an approximate concentration or an approximate range of concentrations for *Listeria* or for a type of *Listeria* such as *Listeria innocua*.

At step 414, the particle of interest prediction module 358 obtains a confidence value for the particle of interest in the sample. In some embodiments, the particle of interest prediction module 358 utilizes the following Python code to obtain the confidence score:

y_score=model·predict_proba(x_test)

In this code, y_score is the confidence value, which may be a float that ranges between zero, inclusive, and one, inclusive. The closer the value is to zero the higher the degree of confidence that the result is negative, and the closer the value is to one the higher the degree of confidence that the result is positive. In some embodiments, the confidence value may be expressed as a percentage between 0% and 100%, inclusive.

At step 416, the notification module 360 generates a particle of interest detection notification that indicates either the positive particle of interest detection or the negative particle of interest detection for the particle of interest in the sample. In some embodiments, the particle of interest detection notification further indicates the approximate concentration or the approximate range of concentrations for the particle of interest in the sample. In some embodiments, the particle of interest detection notification further indicates the confidence value for the particle of interest in the sample. In some embodiments, if the confidence value is within a certain range or above or below a certain threshold, the particle of interest detection notification may include a flag indicating such. For example, if the confidence value is below a certain threshold, the particle of interest detection notification may flag that there is low confidence in the result. As another example, if the confidence value is above a certain threshold, the particle of interest detection notification may flag that there is high confidence in the result.

At step 418, the notification module 360 provides the particle of interest detection notification. In some embodiments, the notification module 360 provides the particle of interest detection notification to the computing device 110 for display by the user interface module 310. The notification module 360 may provide the particle of interest detection notification for display by other digital devices. At step 420, the notification module 360 generates and provides reports, such as dashboards, spreadsheets, or the like, that include results, confidence scores, and/or other information.

In some embodiments, the particle of interest prediction module 358 may apply a third trained model to at least one of the set of spectral metrics and the set of values based on the set of spectral metrics to obtain a third result. The third trained model may be trained on a fifth set of training samples for third particles of interest. In such embodiments, a subset of the fifth set of training samples for the third particles of interest may contain the third particles at a third concentration and a subset of the fifth set of training samples may contain the third particles of interest at a fourth concentration different from the third concentration. The third particles of interest may be different from the first particles of interest and the second particles of interest. For example, the first particles of interest may be *Listeria*, the second particles of interest may be *E. coli* and the third particles of interest may be *Salmonella*.

Further in such embodiments, the particle of interest prediction module 358 may, based on the third result, determine either a second positive particle of interest detection or a second negative particle of interest detection for the third particles of interest in the sample. The particle of interest prediction module 358 may also generate a second particle of interest on notification that indicates either a second positive particle of interest detection or a second negative particle of interest detection for the third particles of interest in the sample. The notification module 360 may also provide the second particle of interest detection notification.

In some embodiments, the set of spectral metrics is a first set of spectral metrics. In such embodiments, the communication module 302 may receive data including at least one second set of spectral metrics from the computing device 110. The at least one second set of spectral metrics are or are based on at least one second interactions of electromagnetic radiation obtained by the spectral acquisition apparatus 102. For example, the spectral acquisition apparatus 102 may perform multiple scans of the sample and provide data including the multiple sets of spectral metrics to the particle of interest detection system 104 via the computing device 110. The particle of interest detection system 104 may thus perform step 402 through step 420 of the method 400 and thus obtain multiple results.

Further in such embodiments, the particle of interest detection system 104 may then determine either the positive particle of interest detection or the negative particle of interest detection for the particle of interest in the sample based on the multiple results. For example, if the particle of interest detection system 104 obtains three results, the particle of interest detection system 104 may determine either the positive particle of interest detection or the negative particle of interest detection for the particle of interest in the sample based on the two results that have the highest confidence score. As another example, if the particle of interest detection system 104 obtains three results, the particle of interest detection system 104 may determine either the positive particle of interest detection or the negative particle of interest detection for the particle of interest in the sample based on the best two results of the three results. It will be understood that the particle of interest detection system 104 may determine either the positive particle of interest detection or the negative particle of interest detection for the particle of interest in the sample in various ways.

FIG. 5 is a flowchart showing a method 500 for training machine learning or artificial intelligence models for detecting particles of interest in some embodiments. Various modules of the particle of interest detection system 104 may perform the method 500. In some embodiments, various modules of the computing device 110 performs the method 500. In some embodiments, various modules of both the computing device 110 and the particle of interest detection system 104 perform the method 500. Although portions of the accompanying description may describe training machine learning or artificial intelligence models for detecting foodborne pathogens, it will be appreciated that sets of decision trees may be trained to detect any particle of interest. Further, it will be appreciated that other machine learning and/or artificial intelligence models, such as convolutional neural networks, may be trained to detect particles of interest, such as foodborne pathogens, pathogens that infect humans, and an environmental pathogens.

In some embodiments, a person, such as a laboratory technician, prepares a set of training samples. One or more particles of interest, that may be foodborne pathogen(s), such as *Listeria innocua, Salmonella, E. coli*, or *Staphylococcus aureus*, may be cultivated in a solution, such as tryptic soy broth (TSB) solution. For example, the set of training samples may include both *Listeria mono* and *Listeria innocua*. The initial concentration of the particle(s) of interest in the solution may be approximately 1e8 colony-forming units/milliliter (cfu/mL). In some embodiments, the initial concentration of the particle(s) of interest in the solution may range from approximately 1e6 to approximately 1e8 cfu/mL. In some embodiments, the initial concentration of the particle of interest in the solution may be greater than approximately 1e8 cfu/mL. In some embodiments, the initial concentration of the particle of interest in the solution may be lower than approximately 1e8 cfu/mL.

A first subset of training samples at the initial concentration of approximately $1e^8$ cfu/mL may be prepared. A second subset of training samples may be prepared that have been diluted 10:1 from the initial concentration using the solution, so as to have a second concentration of approximately $1e^7$ cfu/mL. A third subset of training samples may be prepared that have been diluted 100:1 from the initial concentration using the solution, so as to have a third concentration of approximately $1e^6$ cfu/mL. A fourth subset of training samples may be prepared that have been diluted 1000:1 from the initial concentration using the solution, so as to have a fourth concentration of approximately $1e^5$ cfu/mL. A fifth subset of training samples may be prepared that have been diluted 10,000:1 from the initial concentration using the solution, so as to have a fifth concentration of approximately $1e^4$ cfu/mL. A sixth subset of training samples may be prepared that have been diluted 100,000:1 from the initial concentration using the solution, so as to have a sixth concentration of approximately $1e^3$ cfu/mL. A seventh subset of training samples may be prepared that have been diluted 1,000,000:1 from the initial concentration using the solution, so as to have a seventh concentration of approximately $1e^2$ cfu/mL. An eighth subset of training samples may be prepared that have been diluted 10,000,000:1 from the initial concentration using the solution, so as to have an eighth concentration of approximately 1 cfu/mL. A ninth subset of training samples may be prepared that contain only the solution, for example, the TSB solution.

In some embodiments, there may be fewer than or more than eight subsets of training samples at different concentrations. In some embodiments, the different subsets of training samples may be diluted using different dilution ratios to obtain different concentrations than those described herein. In some embodiments, the set of training samples contains approximately 2000 training samples that include particle(s) of interest, which may be referred to herein as positive training samples. In some embodiments, the set of training samples contains fewer than 2000 positive training samples. In some embodiments, the set of training samples contains more than 2000 positive training samples. In some embodiments, the set of training samples contains approximately the same number of training samples that do not include particle(s) of interest, which may be referred to herein as negative training samples, as the number of positive training samples. In some embodiments, the number of negative training samples is less than the number of positive training samples. In some embodiments, the number of negative training samples is more than the number of positive training samples.

In some embodiments, the set of training samples is prepared prior to the spectral acquisition apparatus 102 scanning the training samples. In some embodiments, the first subset of training samples at the initial concentration of approximately $1e^8$ cfu/mL are prepared and scanned by the spectral acquisition apparatus 102. Then, the first subset of training samples is diluted 10:1 from the initial concentration to obtain the second subset of training samples at the second concentration of approximately $1e^7$ cfu/mL, and then the second subset of training samples is scanned by the spectral acquisition apparatus 102. This dilution and scanning may be repeated several times to obtain, and then scan, the third through eighth subsets of training samples.

To scan a training sample, the cuvette 206 or other suitable container may be filled with a training sample and placed in an appropriate receptacle of the spectral acquisition apparatus 102. The person may then start a scan of the training sample using an interface of the spectral acquisition apparatus 102. Additionally or alternatively, the person may start the scan using a computing device 110, which may control the spectral acquisition apparatus 102. The spectral acquisition apparatus 102 may generate electromagnetic radiation that interacts with the training sample. For example, the spectral acquisition apparatus 102 may generate light that passes through at least a portion of the training sample in the cuvette 206 and detect the light that has passed through at least the portion of the training sample in the cuvette 206. The spectral acquisition apparatus 102 may measure the intensities of the detected light for a set of wavelengths of the light and obtains a set of intensity measurements for the set of wavelengths of the light. The spectral acquisition apparatus 102 may convert the intensity measurements in the set of intensity measurements to other values, such as absorbance values, transmittance values, reflection values, scattered values or concentration values.

In some embodiments, the set of wavelengths of light includes wavelengths of light in the ultraviolet, visible, and infrared spectrums. In some embodiments, the set of wavelengths of light includes wavelengths of light ranging from approximately 300 nanometers (nm) (for example, approximately 320 nm) to approximately 1100 nm (for example, approximately 1100 nm). In some embodiments, the spectral acquisition apparatus 102 has a resolution of 1 nm and obtains a set of 781 intensity measurements for a set of 781 wavelengths of the light. The spectral acquisition apparatus 102 obtains a set of spectral metrics based on interactions of the electromagnetic radiation with the training sample.

Additionally or alternatively, the spectral acquisition apparatus 102 may measure absorbance, transmittance, reflectance and/or scattering of electromagnetic radiation to obtain the set of spectral metrics. The electromagnetic radiation generated by the spectral acquisition apparatus 102 may include ultraviolet light, visible light, and/or infrared light. The spectral acquisition apparatus 102 may also utilize electromagnetic radiation from portions of the electromagnetic spectrum other than ultraviolet, visible, and infrared portions.

The method 500 begins at step 502 where the communication module 352 receives multiple first sets of data from the spectral acquisition apparatus 102 via the computing device 110 for the first subset of training samples containing the particle(s) of interest at the first concentration. The multiple first sets of data include multiple first sets of spectral metrics. A set of spectral metrics may be or be based on a set of intensity measurements for a set of wavelengths of light that the spectral acquisition apparatus 102 obtained. Additionally or alternatively, the set of spectral metrics may be or be based on absorbance, transmittance, reflectance and/or scattering measurements that the spectral acquisition apparatus 102 obtains.

Step 502 may be performed for each subset of training samples containing the particle(s) of interest at a different concentration. That is, the communication module 352 may perform step 502 for the first subset of training samples at the first concentration of approximately $1e^8$ cfu/mL, for the second subset of training samples at the second concentration of approximately $1e^7$ cfu/mL, up to and including for the eighth subset of training samples at the eighth concentration of approximately 1 cfu/mL.

Figure 11A:
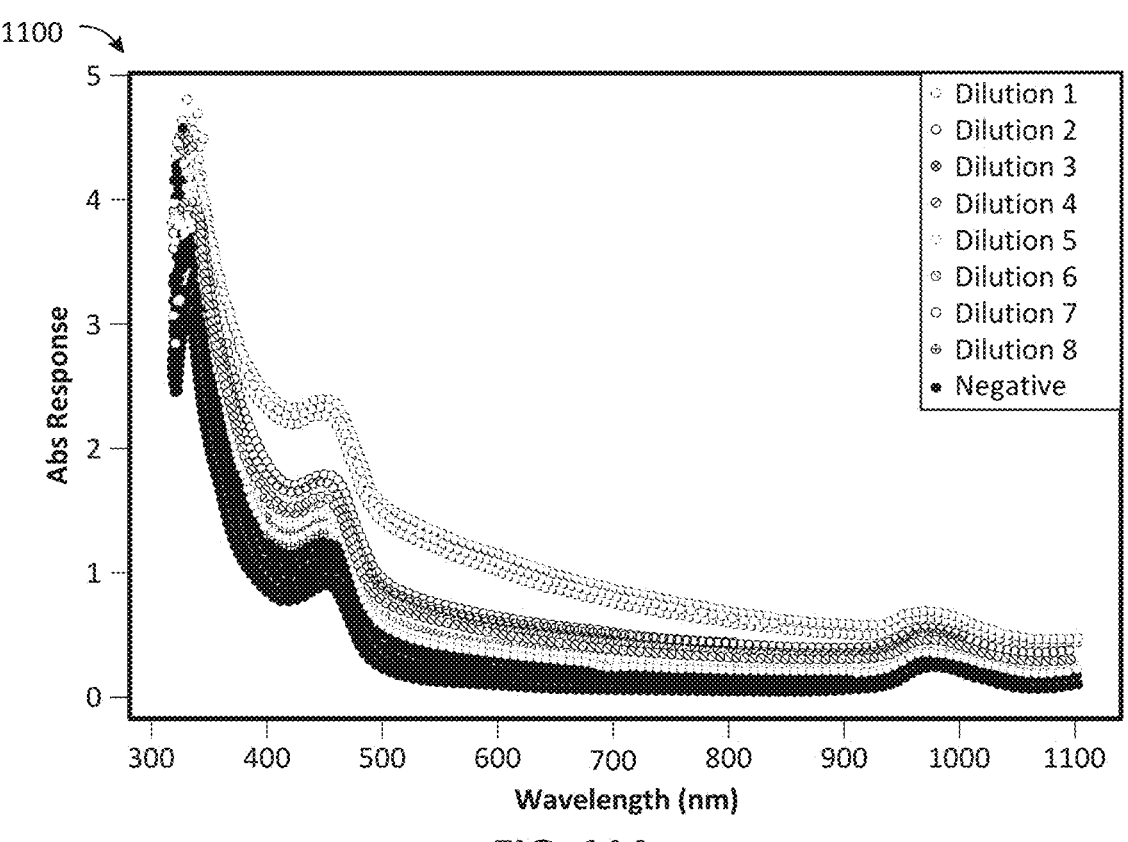
FIG. 11A depicts a graph of absorbance for a set of wavelengths for multiple instances of light that passed through multiple samples containing different concentrations of *Listeria mono* with green fluorescent protein and multiple samples that do not contain *Listeria mono* with green fluorescent protein in some embodiments.

FIG. 11A depicts a graph 1100 of absorbance for a set of wavelengths for multiple instances of light that passed through multiple samples containing different concentrations of *Listeria mono* with green fluorescent protein and multiple samples that do not contain *Listeria mono* with green fluorescent protein in some embodiments. The wavelengths of light range from approximately 320 nm to approximately 1100 nm. The graph 1100 shows the absorbance by wavelength for multiple training samples containing *Listeria mono* with green fluorescent protein at a first concentration (Dilution 1), multiple training samples containing *Listeria mono* with green fluorescent protein at a second concentration lower than the first concentration (Dilution 2), multiple training samples containing *Listeria mono* with green fluorescent protein at a third concentration lower than the second concentration (Dilution 3), multiple training samples containing *Listeria mono* with green fluorescent protein at a fourth concentration lower than the third concentration (Dilution 4), multiple training samples containing *Listeria mono* with green fluorescent protein at a fifth concentration lower than the fourth concentration (Dilution 5), multiple training samples containing *Listeria mono* with green fluorescent protein at a sixth concentration lower than the fifth concentration (Dilution 6), multiple training samples containing *Listeria mono* with green fluorescent protein at a seventh concentration lower than the sixth concentration (Dilution 7), multiple training samples containing *Listeria mono* with green fluorescent protein at an eighth concentration lower than the seventh concentration (Dilution 8), and multiple training samples that do not contain *Listeria mono* with green fluorescent protein (Negative). The graph 1100 illustrates that the absorbance across the range of wavelengths generally decreases as the concentration of *Listeria mono* with green fluorescent protein in a training sample decreases, or conversely, that the absorbance generally increases as the concentration of *Listeria mono* with green fluorescent protein in a training sample increases.

Figure 11B:
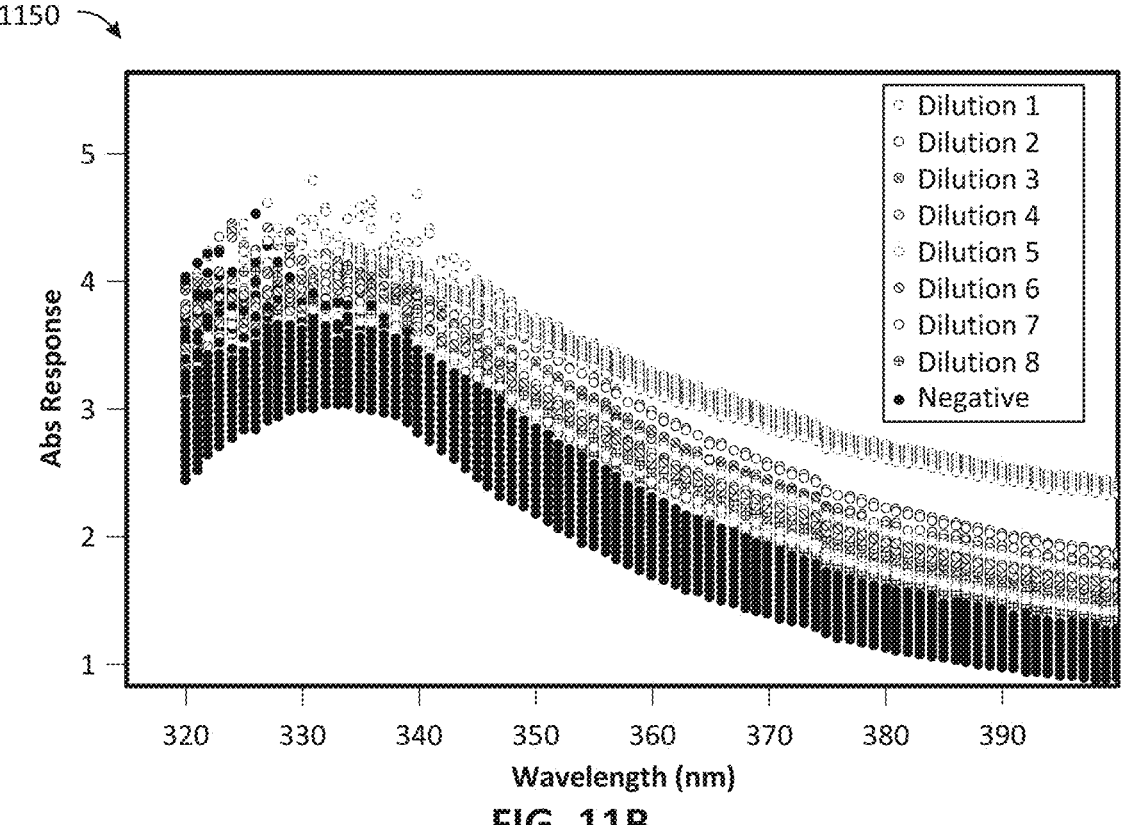
FIG. 11B depicts a graph showing a portion of the set of wavelengths depicted in the graph of FIG. 11A.

FIG. 11B depicts a graph 1150 showing a portion of the set of wavelengths depicted in the graph of FIG. 11A. The wavelengths of light shown in the graph 1150 range from approximately 320 nm to approximately 400 nm.

Figures 13A, 13B:
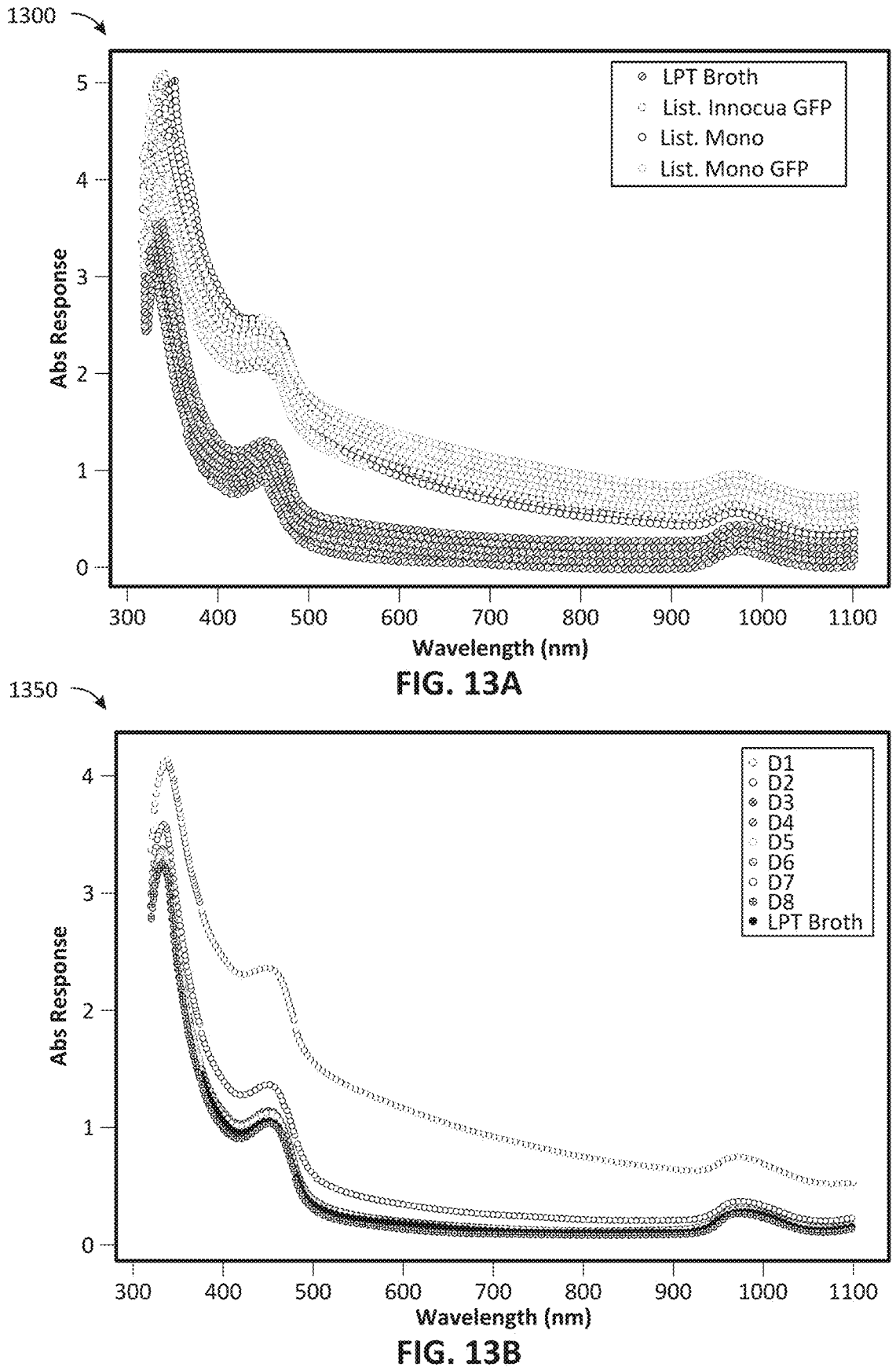
FIG. 13A depicts a graph of absorbance for a set of wavelengths for multiple instances of light that passed through multiple samples containing LPT broth, multiple samples containing *Listeria innocua* with green fluorescent protein, multiple samples containing *Listeria mono*, or multiple samples containing *Listeria mono* with green fluorescent protein in some embodiments.
FIG. 13B depicts a graph of average absorbance for a set of wavelengths for multiple instances of light that passed through multiple samples containing different concentrations of *Listeria mono* or multiple samples that contain LPT broth in some embodiments.

FIG. 13B depicts a graph 1350 of average absorbance for a set of wavelengths for multiple instances of light that passed through multiple samples containing different concentrations of *Listeria mono* or multiple samples that contain LPT broth in some embodiments. The graph 1350 illustrates that the absorbance across the range of wavelengths generally decreases as the concentration of *Listeria mono* in a training sample decreases, or conversely, that the absorbance generally increases as the concentration of *Listeria mono* in a training sample increases.

Returning to FIG. 5, at step 504, the processing module 354 generates multiple first sets of values based on the multiple first sets of spectral metrics. In some embodiments, the processing module 354 normalizes each value in the first set of values to be between zero, inclusive, and one, inclusive. The processing module 354 may further process the values in the first set of values. For example, the processing module 354 may apply a fitting function to each normalized value in the first set of values. In some embodiments, the processing module 354 applies a smoothing filter, such as a Savitzky-Golay filter utilizing a second-order polynomial, to the normalized values. In some embodiments, the Savitzky-Golay filter utilizes a window having a size of 151. The processing module 354 may apply a Savitzky-Golay filter utilizing polynomials of other orders and/or of other window sizes. In some embodiments, the processing module 354 applies a rolling average to the set of values utilizing a window size of 10 and a slide value of 1. The processing module 354 may apply a rolling average utilizing other windows of other sizes and/or other slide values. In some embodiments, the processing module 354 applies other fitting functions and/or signal processing techniques to smooth out the values in the first set of values and/or reduce noise in the values in the first set of values.

Step 504 may be performed for each subset of training samples containing the particle(s) of interest at a different concentration. That is, the processing module 354 may perform step 504 for the first subset of training samples at the first concentration of approximately 1e8 cfu/mL, for the second subset of training samples at the second concentration of approximately 1e7 cfu/mL, up to and including for the eighth subset of training samples at the eighth concentration of approximately 1 cfu/mL.

At step 506, the communication module 352 receives multiple second sets of data from the spectral acquisition apparatus 102 via the computing device 110 for the subset of training samples that do not contain the particle(s) of interest. The multiple second sets of data include multiple second sets of spectral metrics.

At step 508 the processing module 354 generates multiple second sets of values based on the multiple second sets of spectral metrics. In some embodiments, the processing module 354 normalizes each value in the second set of values to be between zero, inclusive, and one, inclusive. The processing module 354 may further process the values in the second set of values. For example, the processing module 354 may apply a fitting function to each normalized value in the second set of values. In some embodiments, the processing module 354 applies a smoothing filter, such as a Savitzky-Golay filter utilizing a second-order polynomial, to the normalized values. In some embodiments, the Savitzky-Golay filter utilizes a window having a size of 151. The processing module 354 may apply a Savitzky-Golay filter utilizing polynomials of other orders and/or of other window sizes. In some embodiments, the processing module 354 applies a rolling average to the set of values utilizing a window size of 10 and a slide value of 1. The processing module 354 may apply a rolling average utilizing other windows of other sizes and/or other slide values. In some embodiments, the processing module 354 applies other fitting functions and/or signal processing techniques to smooth out the values in the second set of values and/or reduce noise in the values in the second set of values.

At step 510, the training and curation module 356 prepares training data based on the multiple second sets of values and the multiple second sets of values. The training and curation module 356 also prepares training labels for the training data. In embodiments where the trained machine learning or artificial intelligence models include a set of trained decision trees and the set of trained decision trees operate in a binary mode, a training label may be either a zero (0) for a negative training sample and a one (1) for a positive training sample. In embodiments where the set of trained decision trees operate in a multiclass mode, a training label may be either a zero (0) for a negative training sample, a one (1) for a positive training sample having a particle of interest concentration at a first concentration, a two (2) for a positive training sample having a particle of interest concentration at a second concentration, a three (3) for a positive training sample having a particle of interest concentration at a third concentration, a four (4) for a positive training sample having a particle of interest concentration at a fourth concentration, a five (5) for a positive training sample having a particle of interest concentration at a fifth concentration, a six (6) for a positive training sample having a particle of interest concentration at a sixth concentration, a seven (7) for a positive training sample having a particle of interest concentration at a seventh concentration, and an eight (8) for a positive training sample having a particle of interest concentration at an eighth concentration. In some embodiments, there are fewer than eight different concentrations of the particle of interest in the training samples and a corresponding lower number of different training labels. In some embodiments, there are more than eight different concentrations of the particle of interest in the training samples and a corresponding higher number of different training labels. The training and curation module 356 may also prepare training data based on different particles of interest at the same or varying concentrations (for example, training data for *E. coli, Listeria innocua, Listeria mono, Salmonella,* etc.).

At step 512, the training and curation module 356 trains the machine learning or artificial intelligence models for the particle(s) of interest. In some embodiments, the training and curation module 356 trains one or more sets of decision trees for the particle(s) of interest. In some embodiments, the training and curation module 356 utilizes an optimized distributed gradient boosting library, XGBoost. In some embodiments, the training and curation module 356 utilizes the following Python code to create each set of decision trees:

```
from xgboost import XGBClassifier
params = {"booster": "gbtree",
    "objective":"binary:logistic",
    "max_delta_step":20,
    "eval_metric":"error",
    "n_estimators": 10000,
    "verbosity":0,
    "max_depth":500,}
self.config.params = params
model = XGBClassifier( **params)
```

XGBClassifier may be understood as a single model that is an ensemble of 10,000 decision trees (the "n_estimators": 10000 parameter). In some embodiments, the training and curation module 356 may utilize parameters other than or in addition to those listed herein. In some embodiments, the training and curation module 356 may utilize different values for model parameters than those listed herein.

In some embodiments, the training and curation module 356 utilizes the following Python code to train each set of the multiple sets of decision trees:

model.fit(x_train, y_train, eval_set=[(x_train, y_train), (x_test, y_test)], early_stopping_rounds=50)

In this code, x_train is training data, y_train is training labels, x_test is testing data, and y_test is testing labels. Both x_train and x_test are ground truth data. Both x_train and x_test may include both positive training samples and negative training samples. In some embodiments, both the x_train and x_test data are balanced, meaning that they include equal or generally equal numbers of positive training samples and negative training samples. In some embodiments, the x_train and x_test data may be imbalanced toward negative training samples, meaning that they include more negative training samples than positive training samples. The training and curation module 356 may also use data sets that are imbalanced towards positive training samples, meaning that they include more positive training samples than negative training samples.

The set of trained decision trees may operate in a binary mode or a multiclass mode. The following Python code may be utilized to determine which mode the set of trained decision trees may operate in:

```
# if binary, set binary, otherwise, set multiclass
if np.max(y_train) == 1:
    params['objective'] = "binary:logistic"
    params['eval_metric'] = 'error'
elif np.max(y_train) > 1:
    params ['objective'] = "multi: softmax"
    params ['eval_metric'] = 'merror'
```

At step 514, the training and curation module 356 validates the set of trained decision trees. In some embodiments, the training and curation module 356 utilizes both training data and testing data to validate the set of trained decision trees. In some embodiments, the training and curation module 356 utilizes only testing data to validate the set of trained decision trees.

In some embodiments, the training and curation module 356 performs the method 500 for each of multiple particles of interest. That is, the training and curation module 356 trains one or more machine learning or artificial intelligence models, such as a set of decision trees, for each of multiple particles of interest, such as *E. coli, Salmonella, Listeria innocua*, and *Staphylococcus aureus*. In some embodiments, the training and curation module 356 may train one or more machine learning or artificial intelligence models, such as a set of decision trees, for each of the following foodborne pathogens: norovirus, *Salmonella* (non-typhoidal), *Clostridium perfringens, Campylobacter, Staphylococcus aureus, Toxoplasma gondii, Escherichia coli (E. coli), Clostridium botulinum, Cryptosporidium, Cyclospora*, hepatitis A virus, *Shigella, Yersinia*, and *Listeria monocytogenes (Listeria)*. The particle of interest prediction module 358 may apply one or more of the trained sets of decision trees to detect particles of interest. Accordingly, the particle of interest detection system 104 may provide panel detection and notification for various particles of interest. One advantage of the particle of interest detection system 104 is that it may provide results for such panel tests quickly (e.g., within seconds or minutes). Another advantage of the particle of interest detection system 104 is that it obviates the need for sending samples to laboratories for test, which may reduce logistical issues and/or complexity.

In various embodiments, a machine learning and/or artificial intelligence architecture may be utilized (e.g., random forest, statistical approaches, and/or the like) in addition to or as an alternative to the sets of decision trees discussed herein. The machine learning and/or AI architecture may utilize the features discussed herein to generate predictive models and/or make predictions. In various embodiments, a 1d or 2d convolutional neural network (CNN) may be used as a discriminator to identify measurements indicating foodborne pathogen contamination and non-foodborne pathogen contamination. In various embodiments, a neural network may be trained using measurements or values from the light intensity measuring apparatuses 102 as discussed herein. The neural network may also be trained using laboratory test results to confirm those foods, equipment, and/or surfaces that are contaminated and those that are not contaminated. The neural network may receive or generate a set of features based on the output (i.e., measurement results or values based thereon) of the light intensity measuring apparatuses 102. The neural network may then be tested to confirm predictions against known foodborne pathogen contamination and non-foodborne pathogen contamination results. In various embodiments, the models may utilize time series data generated by the light intensity measuring apparatuses 102 to make determinations about foodborne pathogen contamination.

In various embodiments, the training and curation module 356 may receive new ground truth data for a particular particle of interest (e.g., new data that includes both positive samples and negative samples for the particular particle of interest) and update the training data and the testing data and retrain the set of decision trees corresponding to the particular particle of interest. For example, the training and curation module 356 may receive new ground truth data for *Salmonella*. The training and curation module 356 may then update the training data and the testing data for *Salmonella* and retrain the set of decision trees for *Salmonella*. This may allow the particle of interest detection system 104 to better detect *Salmonella* in samples of food processing byproducts. The particle of interest detection system 104 may utilize similar processes for other particles of interest such as *E. coli* and *Listeria*. As a result, the ML models and/or AI architecture may be updated, improved, and/or curated based on new positive samples and new negative samples in the new ground truth data.

In some embodiments, the training and curation module 356 may train machine learning or artificial intelligence models, such as sets of decision trees, using training samples from a particular food processing facility, a region that includes multiple food processing facilities, or one or more classes of food processing facilities. This may allow the training and curation module 356 to create sets of trained decision trees that are customized for a particular food processing facility (for example, a single food processing facility), a particular location (for example, food processing facilities located in the Central Valley of California), or a particular type of food processing facility (for example, food processing facilities that slaughter chickens and process slaughtered chickens).

Figure 6:
FIG. 6 is a table showing feature importance for light that passed through one or more samples containing microspheres of different sizes in some embodiments.

FIG. 6 is a table 600 showing feature importance for light that passed through one or more samples containing microspheres of different colors or sizes in some embodiments. For example, wavelengths of 537 nm, 466 nm, 320 nm, 467 nm, and 344 nm may be among the most important wavelengths for detecting 50 nm red microspheres in one or more samples. As another example, wavelengths of 393 nm, 537 nm, 422 nm, 994 nm and 728 nm may be among the most important wavelengths for detecting 50 nm, 500 nm, or 1000 nm red microspheres in one or more samples. As another example, wavelengths of 332 nm, 328 nm, 402 nm, 327 nm, and 1014 nm may be among the most important wavelengths for detecting 1000 nm green microspheres in one or more samples. As another example, wavelengths of 867 nm, 398 nm, 355 nm, 1090 nm, and 466 nm may be among the most important wavelengths for detecting 50 nm, 500 nm, 1000 nm red, green, or a mixture of red and green microspheres. In this last example, the model may have been trained on the different colors of microspheres and not on the size of the microspheres.

Figure 7A:
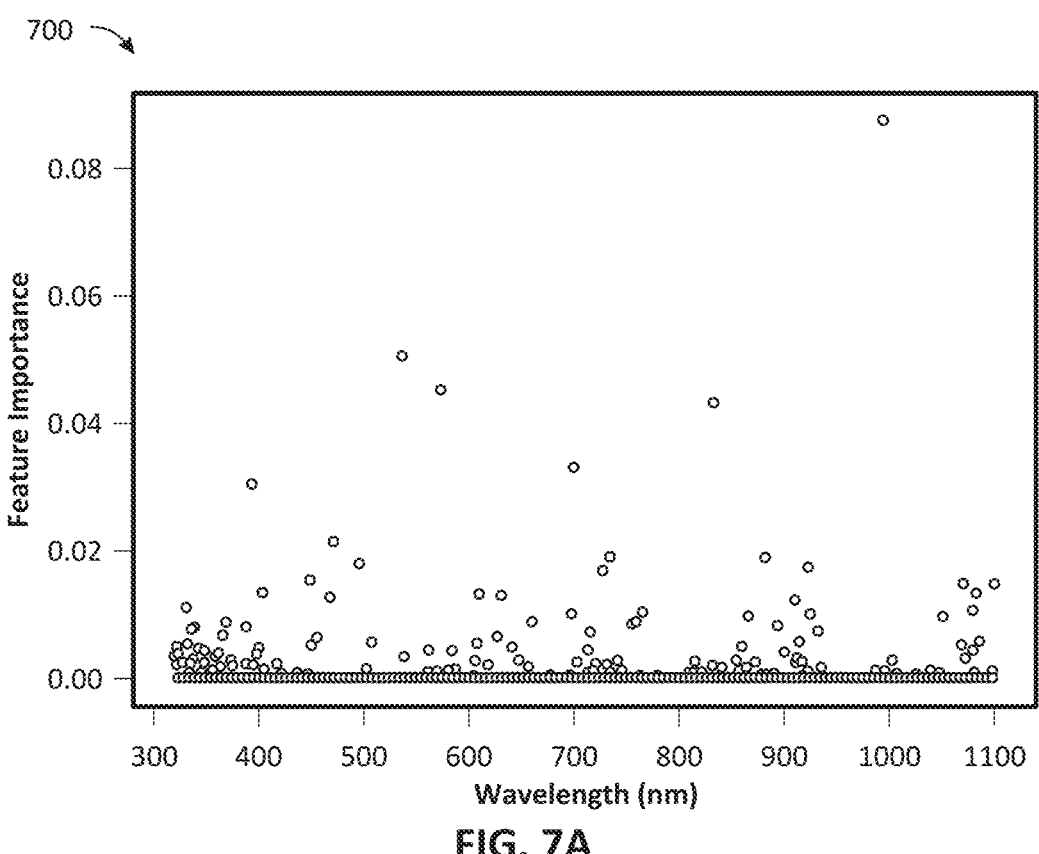
FIGS. 7A and 7B depict graphs of feature importance by wavelength for light that passed through one or more samples containing microspheres of different sizes in some embodiments.
Figure 7B:
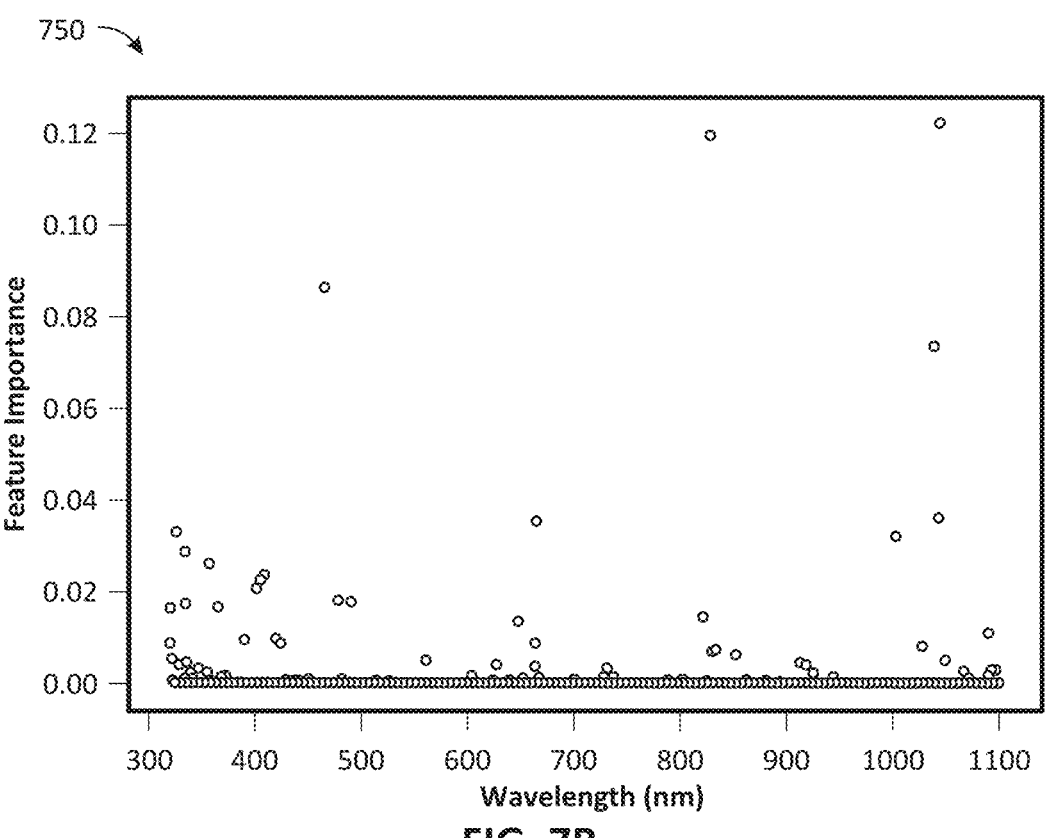

FIGS. 7A and 7B depict graphs of feature importance by wavelength for light that passed through one or more samples containing microspheres of different sizes in some embodiments. FIG. 7A depicts of graph 700 of feature importance by wavelength for light that passed through one or more samples containing 50 nm, 500 nm, or 1000 nm red microspheres. FIG. 7B depicts of graph 750 of feature importance by wavelength for light that passed through one or more samples containing 50 nm, 500 nm, or 1000 nm green microspheres.

Figure 8A:
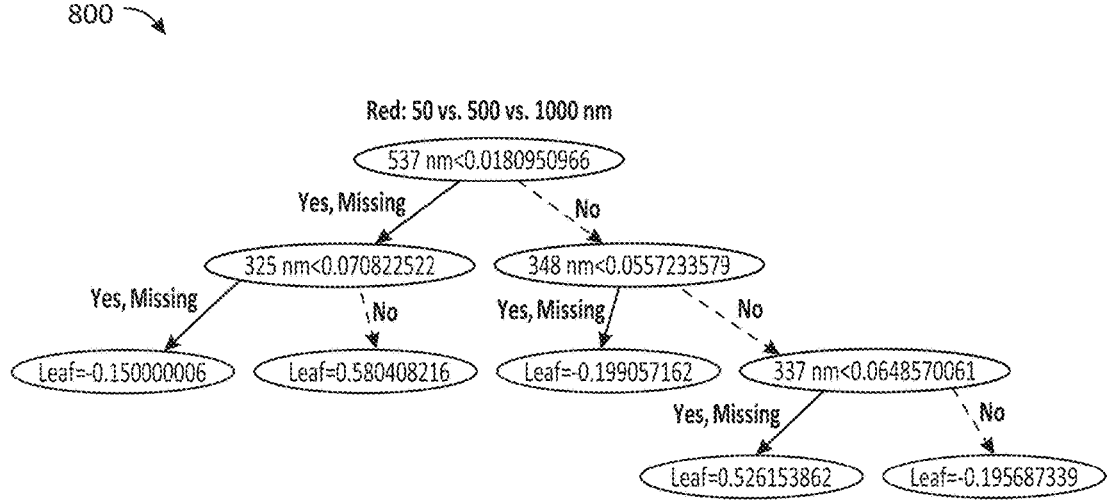
FIGS. 8A and 8B depict portions of example decision trees for detecting microspheres of different sizes in some embodiments.
Figure 8B:
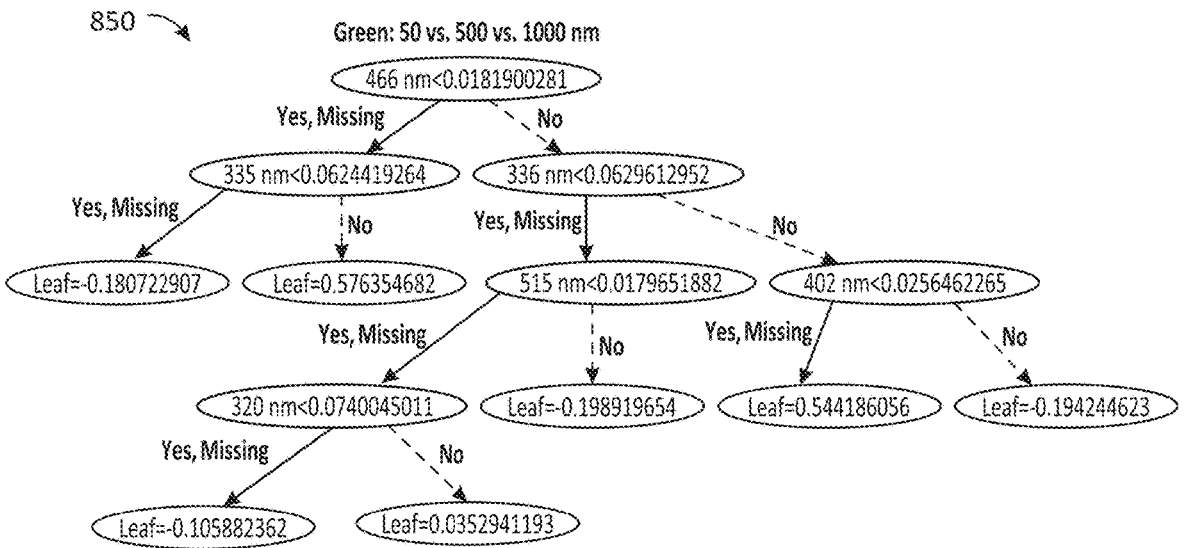

FIGS. 8A and 8B depict portions of example decision trees for detecting microspheres of different sizes in some embodiments. FIG. 8A depicts a portion 800 of a decision tree for detecting 50 nm, 500 nm, or 1000 nm red microspheres. FIG. 8B depicts a portion 850 of a decision tree for detecting 50 nm, 500 nm, or 1000 nm green microspheres.

FIG. 9 is a table 900 showing results for light that passed through one or more samples containing microspheres of different sizes at different concentrations in some embodiments. For example, for red microspheres of size 15 nm at a first concentration (0), a model has an accuracy of 0.76, a specificity of 0.91, and a sensitivity of 0.46. For red microspheres of size 15 nm at a second concentration (1), which may be 10 times as concentrated as the first concentration, a model has an accuracy of 0.908, a specificity of 0.93, and a sensitivity of 0.88.

Figure 10A:
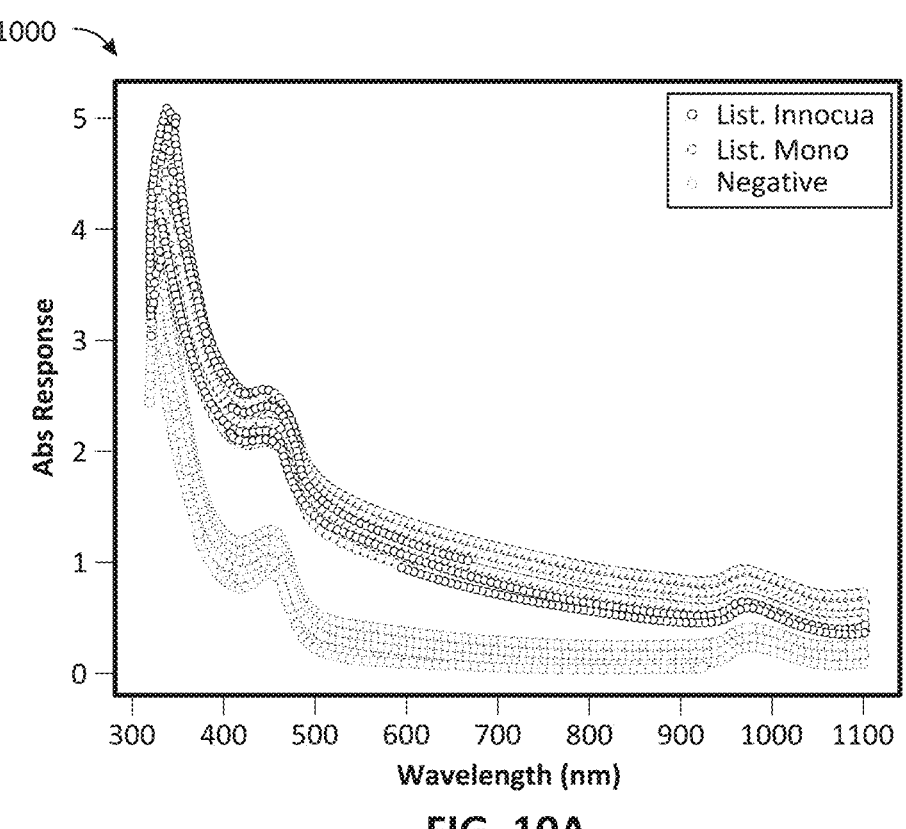
FIG. 10A depicts a graph of absorbance for a set of wavelengths for multiple instances of light that passed through multiple samples containing *Listeria mono*, multiple samples containing *Listeria innocua*, or multiple samples that do not contain *Listeria mono* or *Listeria innocua* in some embodiments.
Figure 10B:
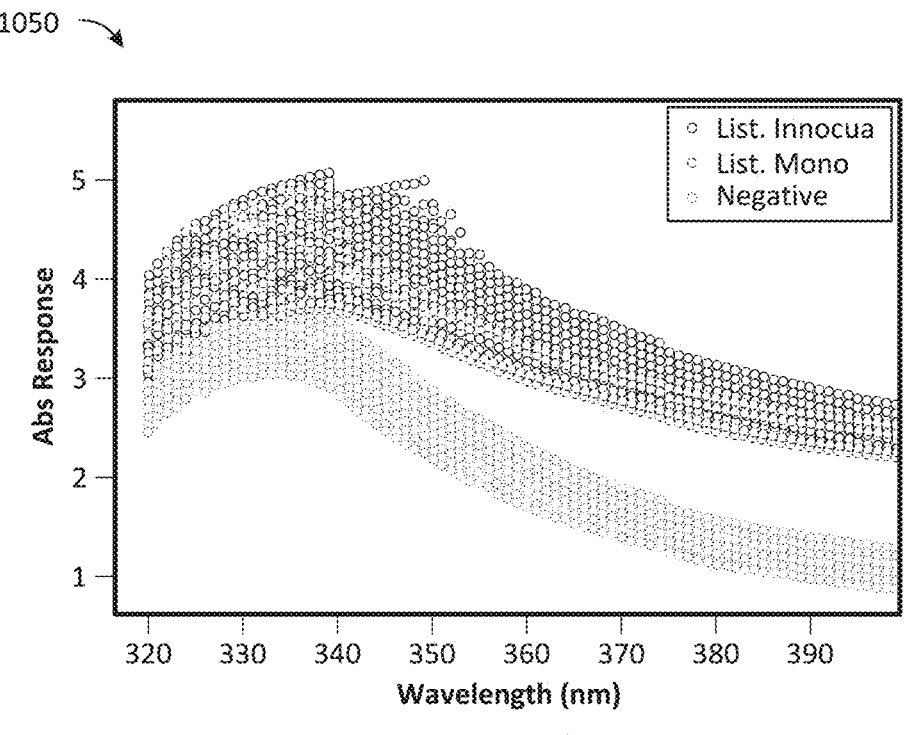
FIG. 10B depicts a graph showing a portion of the set of wavelengths depicted in the graph of FIG. 10A.

FIG. 10A depicts a graph 1000 of absorbance for a set of wavelengths for multiple instances of light that passed through multiple samples containing *Listeria mono* (labeled *List. Mono*), multiple samples containing *Listeria innocua* (labeled *List. Innocua*), or multiple samples that do not contain *Listeria mono* or *Listeria innocua* in some embodiments (labeled negative). The wavelengths of light range from approximately 320 nm to approximately 1100 nm. FIG. 10B depicts a graph 1050 showing a portion of the set of wavelengths depicted in the graph of FIG. 10A. The graphs 1000 and 1050 illustrate that *Listeria innocua* and *Listeria mono* have different absorbance responses than negative samples, particularly at certain wavelengths.

Figure 12A:
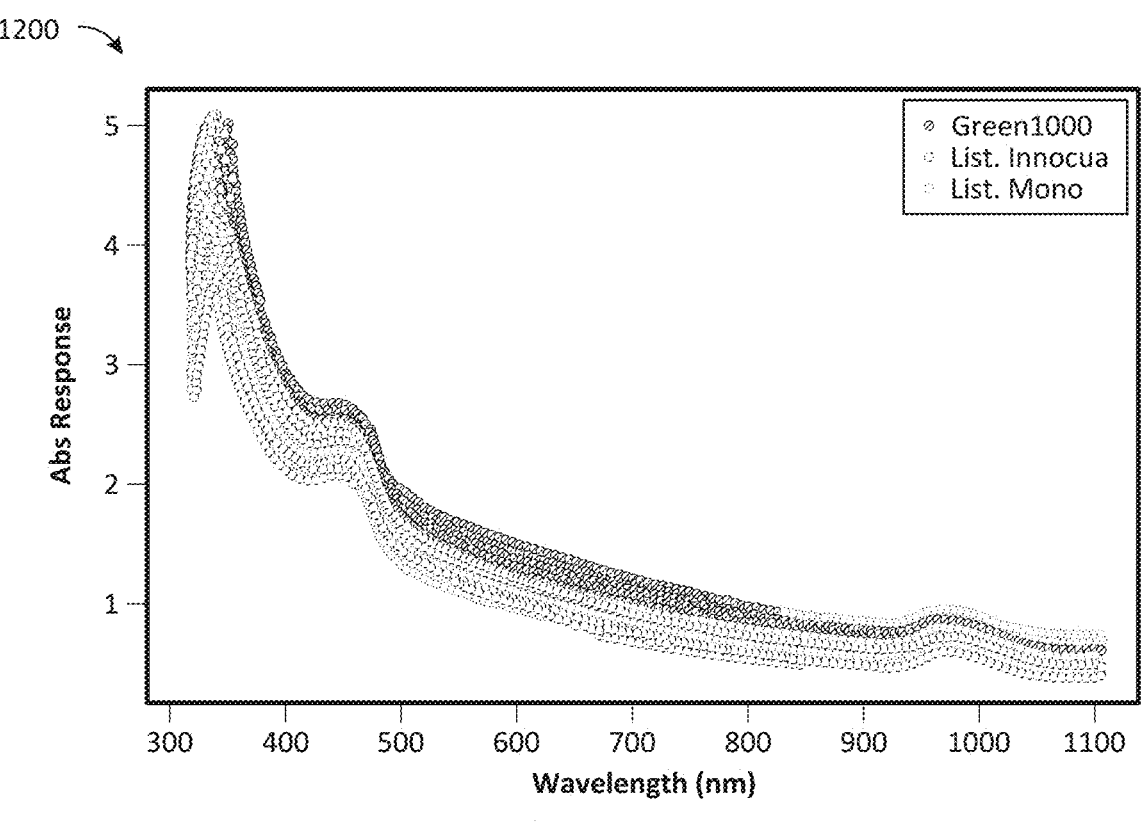
FIG. 12A depicts a graph of absorbance for a set of wavelengths for multiple instances of light that passed through multiple samples containing *Listeria mono*, multiple samples containing *Listeria innocua*, or multiple samples containing green microspheres in some embodiments.

FIG. 12A depicts a graph 1200 of absorbance for a set of wavelengths for multiple instances of light that passed through multiple samples containing *Listeria mono*, multiple samples containing *Listeria innocua*, or multiple samples containing 1000 nm green microspheres in some embodiments. In some embodiments, the model has an approximately 0.983 accuracy for detecting *Listeria mono, Listeria innocua*, or 1000 nm green microspheres.

Figure 14A:
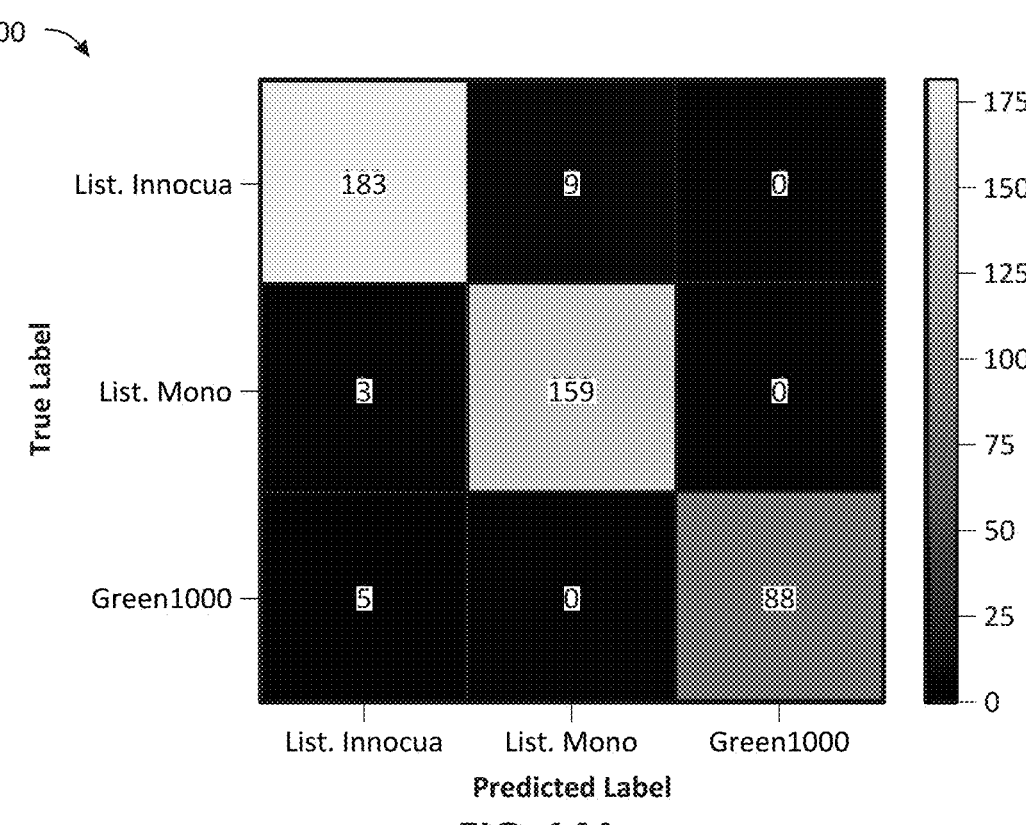
FIG. 14A depicts a confusion matrix for results of applications of a set of trained decision trees to multiple sets of values based on intensity measurements of multiple instances of light that has passed through multiple samples containing *Listeria innocua*, multiple samples containing *Listeria mono*, or multiple samples containing green microspheres in some embodiments.

FIG. 14A depicts a confusion matrix 1400 for results of applications of a set of trained decision trees to multiple sets of values based on intensity measurements of multiple instances of light that has passed through multiple samples containing *Listeria innocua*, multiple samples containing *Listeria mono*, or multiple samples containing 1000 nm green microspheres in some embodiments. The set of trained decision trees that produced the results in the confusion matrix 1400 may have been trained to detect *Listeria innocua, listeria* mono, or 1000 nm green microspheres and may have operated in a multiclass mode. There may have been 447 total testing samples. In the set of testing samples, there may have been 192 testing samples containing *Listeria innocua*, 162 testing samples containing *Listeria mono*, and 93 testing samples containing 1000 nm green microspheres. The trained decision trees may have accurately detected *Listeria innocua* in 183 of the 192 testing samples containing *Listeria innocua, Listeria mono* in 159 of the 162 testing samples containing *Listeria mono*, and 1000 nm green microspheres in 88 of the 93 testing samples containing 1000 nm green micro spheres.

Figure 12B:
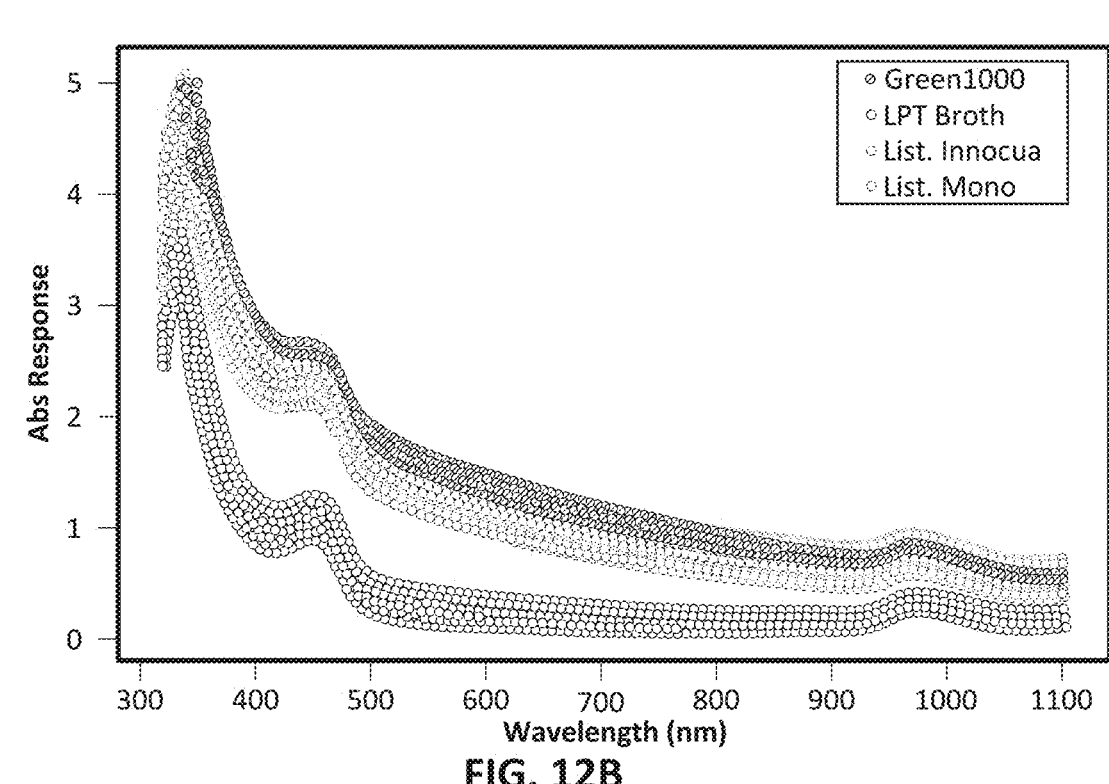
FIG. 12B depicts a graph of absorbance for a set of wavelengths for multiple instances of light that passed through multiple samples containing *Listeria mono*, multiple samples containing *Listeria innocua*, multiple samples containing green microspheres, or multiple samples containing LPT broth in some embodiments.

FIG. 12B depicts a graph 1250 of absorbance for a set of wavelengths for multiple instances of light that passed through multiple samples containing *Listeria mono*, multiple samples containing *Listeria innocua*, multiple samples containing 1000 nm green microspheres, or multiple samples containing LPT broth in some embodiments.

FIG. 13A depicts a graph 1300 of absorbance for a set of wavelengths for multiple instances of light that passed through multiple samples containing LPT broth, multiple samples containing *Listeria innocua* with green fluorescent protein, multiple samples containing *Listeria mono*, or multiple samples containing *Listeria mono* with green fluorescent protein in some embodiments. In some embodiments, the model has an approximately 0.988 accuracy for detecting LPT broth, *Listeria innocua* with green fluorescent protein, *Listeria mono*, or *Listeria mono* with green fluorescent protein.

Figure 14B:
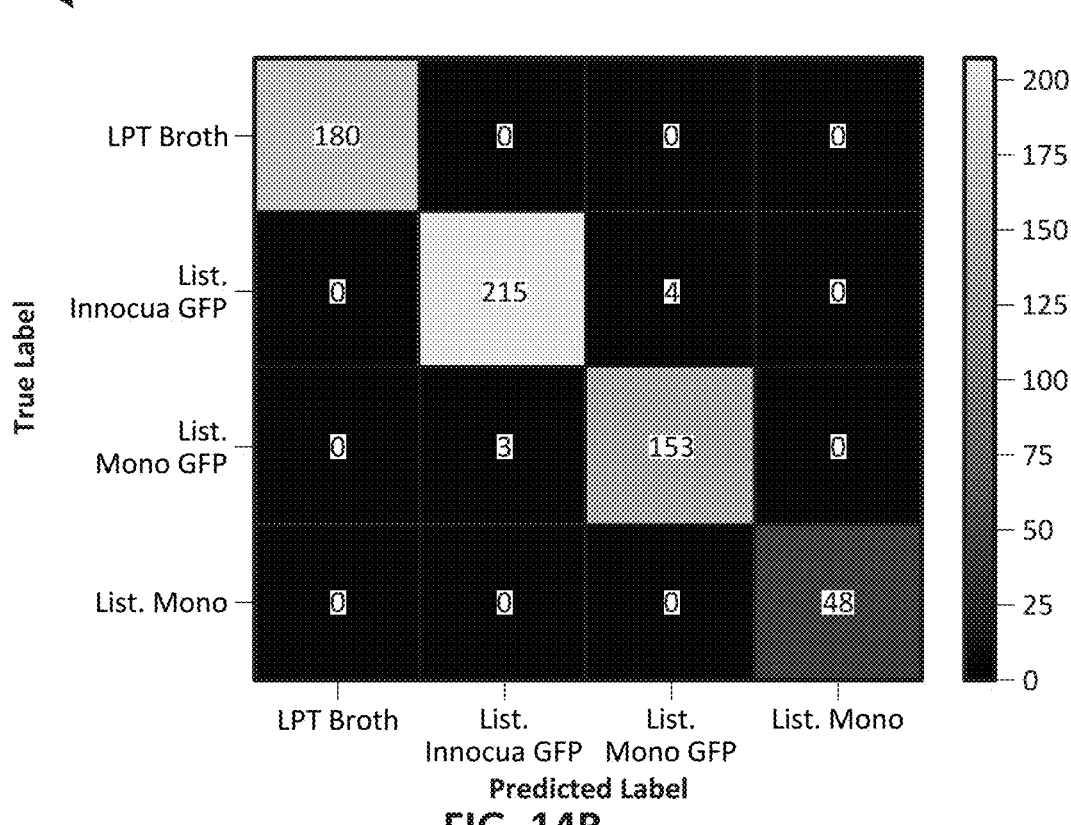
FIG. 14B depicts a confusion matrix for results of applications of a set of trained decision trees to multiple sets of values based on intensity measurements of multiple instances of light that has passed through multiple samples containing LPT broth, multiple samples containing *Listeria innocua* with green fluorescent protein, multiple samples containing *Listeria mono* with green fluorescent protein, or multiple samples containing *Listeria mono* in some embodiments.

FIG. 14B depicts a confusion matrix 1450 for results of applications of a set of trained decision trees to multiple sets of values based on intensity measurements of multiple instances of light that has passed through multiple samples containing LPT broth, multiple samples containing *Listeria innocua* with green fluorescent protein, multiple samples containing *Listeria mono* with green fluorescent protein, or multiple samples containing *Listeria mono* in some embodiments. The set of trained decision trees that produced the results in the confusion matrix 1450 may have been trained to detect LPT broth, *Listeria innocua* with green fluorescent protein, *Listeria mono* with green fluorescent protein, or *Listeria mono* and may have operated in a multiclass mode. There may have been 599 total testing samples. In the set of testing samples, there may have been 180 testing samples containing LPT broth, 219 testing samples containing *Listeria innocua* with green fluorescent protein, 156 testing samples containing *Listeria mono* with green fluorescent protein, and 48 testing samples containing *Listeria mono*. The trained decision trees may have accurately detected LPT broth in 180 of the 180 testing samples containing LPT broth, *Listeria innocua* with green fluorescent protein in 215 of the 219 testing samples containing *Listeria innocua* with green fluorescent protein, *Listeria mono* with green fluorescent protein in 153 of the 156 testing samples containing *Listeria mono* with green fluorescent protein, and *Listeria mono* in 48 of the 48 testing samples containing *Listeria mono*.

Figure 15A:
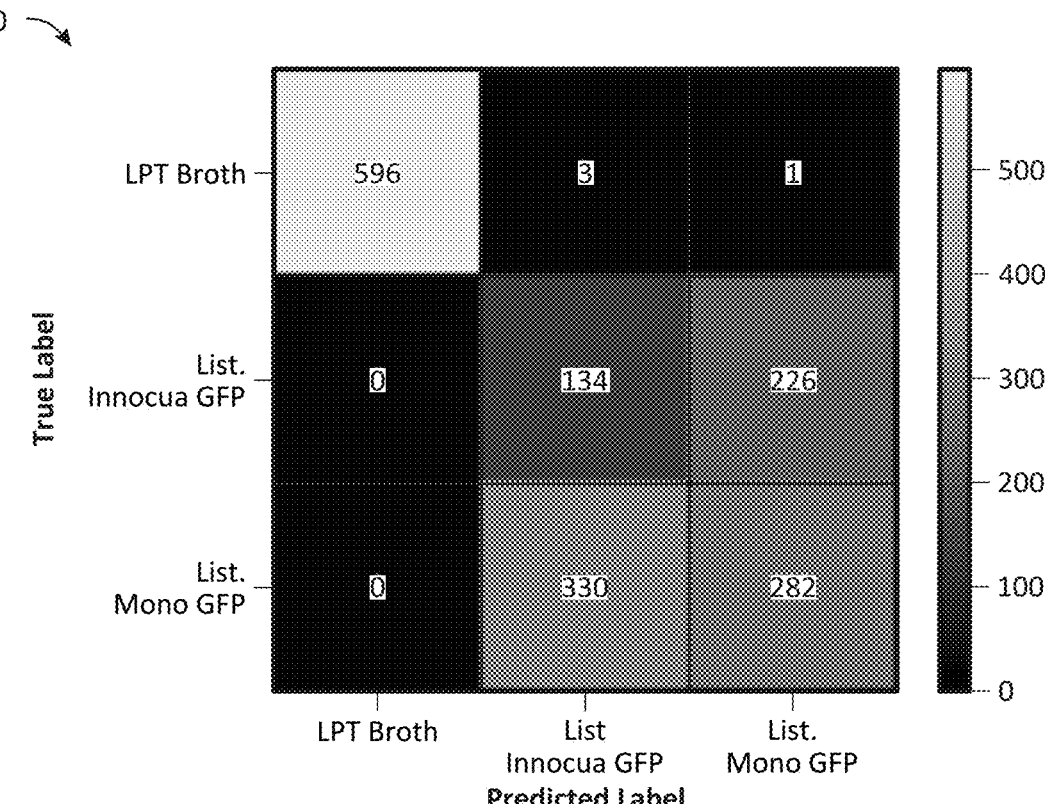
FIG. 15A depicts a confusion matrix for results of applications of a set of trained decision trees to multiple sets of values based on intensity measurements of multiple instances of light that has passed through multiple samples containing LPT broth, multiple samples containing *Listeria innocua* with green fluorescent protein, or multiple samples containing *Listeria mono* with green fluorescent protein in some embodiments.

FIG. 15A depicts a confusion matrix 1500 for results of applications of a set of trained decision trees to multiple sets of values based on intensity measurements of multiple instances of light that has passed through multiple samples containing LPT broth, multiple samples containing *Listeria innocua* with green fluorescent protein, or multiple samples containing *Listeria mono* with green fluorescent protein in some embodiments. The set of trained decision trees that produced the results in the confusion matrix 1500 may have been trained to detect LPT broth, *Listeria innocua* with green fluorescent protein, or *Listeria mono* with green fluorescent protein and may have operated in a multiclass mode. There may have been 1572 total testing samples. In the set of testing samples, there may have been 596 testing samples containing LPT broth, 360 testing samples containing *Listeria innocua* with green fluorescent protein, and 612 testing samples containing *Listeria mono* with green fluorescent protein. The trained decision trees may have accurately detected LPT broth in 596 of the 600 testing samples containing LPT broth, *Listeria innocua* with green fluorescent protein in 134 of the 360 testing samples containing *Listeria innocua* with green fluorescent protein, and *Listeria mono* with green fluorescent protein in 330 of the 612 testing samples containing *Listeria mono* with green fluorescent protein.

Figure 15B:
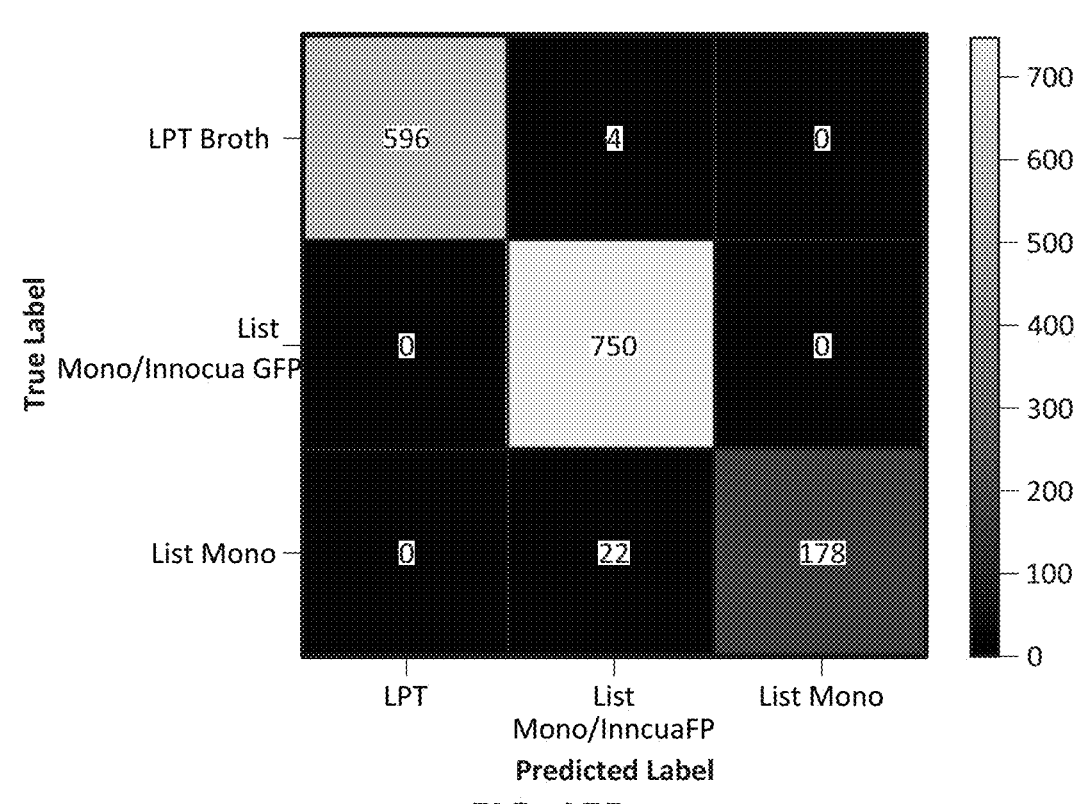
FIG. 15B depicts a confusion matrix for results of applications of a set of trained decision trees to multiple sets of values based on intensity measurements of multiple instances of light that has passed through multiple samples containing LPT broth, multiple samples containing *Listeria mono* or *Listeria innocua* with green fluorescent protein, or multiple samples containing *Listeria mono* in some embodiments.

FIG. 15B depicts a confusion matrix 1550 for results of applications of a set of trained decision trees to multiple sets of values based on intensity measurements of multiple instances of light that has passed through multiple samples containing LPT broth, multiple samples containing *Listeria mono* or *Listeria innocua* with green fluorescent protein, or multiple samples containing *Listeria mono* in some embodiments. The set of trained decision trees that produced the results in the confusion matrix 1500 may have been trained to detect LPT broth, *Listeria mono* or *Listeria innocua* with green fluorescent protein, or *Listeria mono* and may have operated in a multiclass mode. There may have been 1550 total testing samples. In the set of testing samples, there may have been 600 testing samples containing LPT broth, 750 testing samples containing *Listeria mono* or *Listeria innocua* with green fluorescent protein, and 200 testing samples containing *Listeria mono*. The trained decision trees may have accurately detected LPT broth in 596 of the 600 testing samples containing LPT broth, *Listeria mono* or *Listeria innocua* with green fluorescent protein in 750 of the 750 testing samples *Listeria mono* or *Listeria innocua* with green fluorescent protein, and *Listeria mono* in 178 of the 200 testing samples containing *Listeria mono.*

One advantage of the particle of interest detection systems and associated methods described herein is that such systems and methods may be utilized to detect any particles of interest that may affect human or animal health and/or the environment. For example, the particle of interest detection system may be utilized to detect the presence of pathogens that humans or animals such as SARS-CoV-2, COVID-19 or RSV. In some embodiments, the particle of interest detection system and associated methods may be operated to detect particles of interest or pathogens such as the Human Papillomavirus (HPV) infection or other sexually transmitted diseases (STDs) or sexually transmitted infections (STIs).

In another example, the particle of interest detection system and associated methods may be operated to detect pathogens and/or contaminants that may have an environmental effect on air quality. The particle of interest detection system may be utilized to detect the presence of ethylene, methylene, and other volatile organic compounds (VOCs). The particle of interest detection system and associated methods may also be utilized to detect pathogens and/or contaminants that may affect water quality. Accordingly, the particle of interest detection system and associated methods described herein may also aid community water systems and/or other water suppliers with complying with water quality standards, such as those promulgated by government agencies such as the U.S. Environmental Protection Agency.

Another advantage of the particle of interest detection systems and associated methods described herein is that such systems and methods may be utilized to detect multiple different particles of interest using a single set of spectral metrics obtained from a single set of interactions of electromagnetic radiation with a single sample. For example, under previous techniques, to detect COVID-19, influenza, *streptococcus*, and Respiratory Syncytial Virus Infection (RSV), four different swabs and four different expensive and time-consuming tests to may be required. In contrast, the particle of interest detection systems and associated methods may utilize a single swab to obtain a single set of spectral metrics, to which multiple trained models (e.g., a trained model for detecting COVID-19, a trained model for detecting influenza, a trained model for detecting *streptococcus*, and a trained model for detecting RSV) may be applied to detect all four pathogens, and may be able to provide either positive or negative results for each of the four pathogens in a shorter period of time, which may be as short as one or several minutes.

As another example, in the food safety context, under previous techniques, to detect *E. coli, salmonella*, and *Listeria* requires three different swabs and enrichment and incubation in potentially different reagents, which may be expensive. Each test may also require a significant amount of time, such as between approximately 24 to approximately 96 hours, and may be expensive to perform. In contrast, the particle of interest detection systems and associated methods may utilize a single swab to obtain a single set of spectral metrics, to which multiple trained models (e.g., a trained model for detecting *E. coli*, a trained model for detecting influenza, a trained model for detecting *Salmonella*, and a trained model for detecting *Listeria*) may be applied to detect all three foodborne pathogens, and may be able to provide either positive or negative results for each of the three foodborne pathogens in a shorter period of time, which may be as short as one or several minutes.

Accordingly, the particle of interest detection systems and associated methods described herein provide for the ability to perform a panel of tests and obtain results in a shorter period of time than previous techniques allow for.

Another advantage of the particle of interest detection systems and associated methods described herein is that the computing device 110 and the software application 112 may be able to obtain spectral metrics from a wide variety of spectral acquisition apparatuses, such as spectrometers, spectrophotometers, thermal emission spectrometers, cameras, and/or any apparatus that may provide spectral metrics. This may be due in part to the extensibility of the software application 112, which may be configured to interface with a wide variety of spectral acquisition apparatuses. Accordingly, the computing device 110 and the software application 112 may be considered hardware-independent, which may facilitate their placement and usage at different facilities, such as food processing facilities, health care facilities such as hospitals, industrial facilities such as factories, and water treatment facilities such as municipal water treatment facilities.

Yet another advantage of the particle of interest detection systems and associated methods described herein is that the particle of interest detection system 104 may store data, such as metadata, reference data, and results data, that may be analyzed and/or accessed so as to obtain insights into the prevalence of harmful particles of interest, such as foodborne pathogens, infectious pathogens (for example, pathogens that infect humans and/or animals), and/or environmental pollutants and/or contaminants. Such insights may be provided to customers and/or partners of entities utilizing the particle of interest detection systems and associated methods, as well as to governmental agencies occupied with human health and/or safety and/or environmental health, such as the U.S. FDA, the U.S. EPA, and/or the U.S. Department of Health and Human Services. Such insights may be utilized to help prevent and/or reduce threats to human health and/or environmental health. Accordingly, analysis of spectral analysis may provide actionable intelligence of significant value.

Additional details regarding techniques used to detect pathogens using spectrometer scans are described in U.S. patent application Ser. No. 18/173,050 filed on Feb. 22, 2023, and entitled "SYSTEMS AND METHODS FOR DETECTING PATHOGENS USING SPECTROMETER SCANS," the entirety of which is incorporated herein by reference.

Furthermore, additional details regarding techniques used to detect pathogens using spectral analysis are described in U.S. patent application Ser. No. 18/173,035 filed on filed on Feb. 22, 2023, and entitled "SYSTEMS AND METHODS FOR DETECTING FOODBORNE PATHOGENS USING SPECTRAL ANALYSIS," the entirety of which is incorporated herein by reference. Furthermore, additional details regarding techniques used to detect foodborne pathogens by analyzing spectral data are described in U.S. patent application Ser. No. 18/346,749 filed on filed on Jul. 3, 2023, and entitled "SYSTEMS AND METHODS FOR DETECTING FOODBORNE PATHOGENS BY ANALYZING SPECTRAL DATA," and techniques used to detect particles of interest using spectral analysis are described in U.S. patent application Ser. No. 18/358,798 filed on filed on Jul. 25, 2023, and entitled "SYSTEMS AND METHODS FOR DETECTING PARTICLES OF INTEREST USING SPECTRAL ANALYSIS," the entirety of each of which is incorporated herein by reference.

FIG. 16 depicts a block diagram of an example digital device 1600 according to some embodiments. The digital device 1600 is shown in the form of a general-purpose computing device. The digital device 1600 includes at least one processor 1602, RAM 1604, communication interface 1606, input/output device 1608, storage 1610, and a system bus 1612 that couples various system components including storage 1610 to the at least one processor 1602. A system, such as a computing system, may be or include one or more of the digital device 1600.

System bus 1612 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

The digital device 1600 typically includes a variety of computer system readable media, such as computer system readable storage media. Such media may be any available media that is accessible by any of the systems described herein and it includes both volatile and nonvolatile media, removable and non-removable media.

In some embodiments, the at least one processor 1602 is configured to execute executable instructions (for example, programs). In some embodiments, the at least one processor 1602 comprises circuitry or any processor capable of processing the executable instructions.

In some embodiments, RAM 1604 stores programs and/or data. In various embodiments, working data is stored within RAM 1604. The data within RAM 1604 may be cleared or ultimately transferred to storage 1610, such as prior to reset and/or powering down the digital device 1600.

In some embodiments, the digital device 1600 is coupled to a network via communication interface 1606. In some embodiments the particle of interest detection system 104 can communicate with one or more networks such as a local area network (LAN), a general wide area network (WAN), and/or a public network (for example, the Internet).

In some embodiments, input/output device 1608 is any device that inputs data (for example, mouse, keyboard, stylus, sensors, etc.) or outputs data (for example, speaker, display, virtual reality headset).

In some embodiments, storage 1610 can include computer system readable media in the form of non-volatile memory, such as read only memory (ROM), programmable read only memory (PROM), solid-state drives (SSD), flash memory, and/or cache memory. Storage 1610 may further include other removable/non-removable, volatile/non-volatile computer system storage media. By way of example only, storage 1610 can be provided for reading from and writing to a non-removable, non-volatile magnetic media. The storage 1610 may include a non-transitory computer-readable medium, or multiple non-transitory computer-readable media, which stores programs or applications for performing functions such as those described herein with reference to, for example, FIGS. 3A and 3B. Although not shown, a magnetic disk drive for reading from and writing to a removable, non-volatile magnetic disk (for example, a "floppy disk"), and an optical disk drive for reading from or writing to a removable, non-volatile optical disk such as a CDROM, DVD-ROM or other optical media can be provided. In such instances, each can be connected to system bus 1612 by one or more data media interfaces. As will be further depicted and described below, storage 1610 may include at least one program product having a set (for example, at least one) of program modules that are configured to carry out the functions of embodiments of the disclosure. In some embodiments, RAM 1604 is found within storage 1610.

Programs/utilities, having a set (at least one) of program modules, such as the interest detection system 104, may be stored in storage 1610 by way of example, and not limitation, as well as an operating system, one or more application programs, other program modules, and program data. Each of the operating system, one or more application programs, other program modules, and program data or some combination thereof, may include an implementation of a networking environment. Program modules generally carry out the functions and/or methodologies of embodiments of the disclosure as described herein.

It should be understood that although not shown, other hardware and/or software components could be used in conjunction with the digital device 1600. Examples include, but are not limited to microcode, device drivers, redundant processing units, and external disk drive arrays, RAID systems, tape drives, and data archival storage systems, etc.

Exemplary embodiments are described herein in detail with reference to the accompanying drawings. However, the present disclosure can be implemented in various manners, and thus should not be construed to be limited to the embodiments disclosed herein. On the contrary, those embodiments are provided for the thorough and complete understanding of the present disclosure, and completely conveying the scope of the present disclosure.

It will be appreciated that aspects of one or more embodiments may be embodied as a system, method, or computer program product. Accordingly, aspects may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), a solid state drive (SSD), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program or data for use by or in connection with an instruction execution system, apparatus, or device.

A transitory computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object-oriented programming language such as Java, Smalltalk, C++, Python, or the like and conventional procedural programming languages, such as the "C" programming language or similar programming languages. The computer program code may execute entirely on any of the systems described herein or on any combination of the systems described herein.

Aspects of the present disclosure are described below with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

While specific examples are described above for illustrative purposes, various equivalent modifications are possible. For example, while processes or blocks are presented in a given order, alternative implementations may perform routines having steps, or employ systems having blocks, in a different order, and some processes or blocks may be deleted, moved, added, subdivided, combined, and/or modified to provide alternative or sub-combinations. Each of these processes or blocks may be implemented in a variety of different ways. Also, while processes or blocks are at times shown as being performed in series, these processes or blocks may instead be performed or implemented concurrently or in parallel or may be performed at different times. Further any specific numbers noted herein are only examples: alternative implementations may employ differing values or ranges.

Throughout this specification, plural instances may implement components, operations, or structures described as a single instance. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein. Furthermore, any specific numbers noted herein are only examples: alternative implementations may employ differing values or ranges.

Components may be described or illustrated as contained within or connected with other components. Such descriptions or illustrations are examples only, and other configurations may achieve the same or similar functionality. Components may be described or illustrated as "coupled", "couplable", "operably coupled", "communicably coupled" and the like to other components. Such description or illustration should be understood as indicating that such components may cooperate or interact with each other, and may be in direct or indirect physical, electrical, or communicative contact with each other.

Components may be described or illustrated as "configured to", "adapted to", "operative to", "configurable to", "adaptable to", "operable to" and the like. Such description or illustration should be understood to encompass components both in an active state and in an inactive or standby state unless required otherwise by context.

The use of "or" in this disclosure is not intended to be understood as an exclusive "or." Rather, "or" is to be understood as including "and/or." For example, the phrase "providing products or services" is intended to be understood as having several meanings: "providing products," "providing services", and "providing products and services."

It may be apparent that various modifications may be made, and other embodiments may be used without departing from the broader scope of the discussion herein. Therefore, these and other variations upon the example embodiments are intended to be covered by the disclosure herein.

The invention claimed is:

1. A non-transitory computer-readable medium comprising executable instructions, the executable instructions being executable by one or more processors to perform a method, the method comprising:

receiving data, the data including a set of spectral metrics, the data from an apparatus that obtains the set of spectral metrics based on interactions of electromagnetic radiation with a sample;

applying a first trained model to at least one of the set of spectral metrics and a set of values based on the set of spectral metrics to obtain a first result, the first trained model trained on a first set of training samples for first particles of interest and a second set of training samples for second particles of interest, the first particles of interest including at least a first type of the first particles of interest and a second type of the first particles of interest;

applying a second trained model to at least one of the set of spectral metrics and the set of values to obtain a second result, the second trained model being different than the first trained model and trained on a third set of training samples for the first type of the first particles of interest and a fourth set of training samples for the second type of the first particles of interest;

based on at least one of the first result and the second result, determining either a positive particle of interest detection or a negative particle of interest detection for at least one of the first particles of interest, the first type of the first particles of interest, and the second type of the first particles of interest for the sample;

generating a particle of interest detection notification that indicates either the positive particle of interest detection or the negative particle of interest detection; and providing the particle of interest detection notification.

2. The non-transitory computer-readable medium of claim 1 wherein the sample is at least one of a sample of a food processing byproduct, a sample from a person, and an environmental sample, and at least one of the first particles of interest and the second particles of interest includes at least one of a foodborne pathogen, a pathogen that infects humans or animals, and an environmental particle of interest.

3. The non-transitory computer-readable medium of claim 1, the method further comprising normalizing each spectral metric in the set of spectral metrics to be between zero, inclusive, and one, inclusive, to obtain the set of values, and wherein applying the first trained model to at least one of the set of spectral metrics and the set of values based on the set of spectral metrics to obtain the first result includes applying the first trained model to the set of values.

4. The non-transitory computer-readable medium of claim 1, the method further comprising:

training a first model on the first set of training samples for the first particles of interest and the second set of training samples for the second particles of interest to obtain the first trained model; and training a second model on the third set of training samples for the first type of the first particles of interest and the fourth set of training samples for the second type of the first particles of interest to obtain the second trained model.

5. The non-transitory computer-readable medium of claim 1 wherein at least some training samples of at least one of the first set of training samples, the second set of training samples, the third set of training samples, and the fourth set of training samples correspond to a particular food processing facility, a region that includes multiple food processing facilities, or one or more classes of food processing facilities.

6. The non-transitory computer-readable medium of claim 1 wherein spectral metrics in the set of spectral metrics include one of absorbance metrics, transmittance metrics, reflectance metrics, and scattering metrics.

7. The non-transitory computer-readable medium of claim 1 wherein at least one of the first result and the second result indicates the positive particle of interest detection if at least one of the first result and the second result meets or exceeds a threshold.

8. The non-transitory computer-readable medium of claim 1 wherein the electromagnetic radiation includes at least one of ultraviolet light, visible light, and infrared light.

9. The non-transitory computer-readable medium of claim 1 wherein the first trained model includes a first set of trained decision trees, and wherein the second trained model includes a second set of trained decision trees.

10. The non-transitory computer-readable medium of claim 1 wherein the first set of training samples includes a first subset of training samples containing the first particles of interest at a first concentration and a second subset of training samples containing the first particles of interest at a second concentration different from the first concentration, and wherein the second set of training samples includes a third subset of training samples containing the second particles of interest at a third concentration and a fourth subset of training samples containing the second particles of interest at a fourth concentration different from the third concentration.

11. A method comprising:

receiving data, the data including a set of spectral metrics, the data from an apparatus that obtains the set of spectral metrics based on interactions of electromagnetic radiation with a sample;

applying a first trained model to at least one of the set of spectral metrics and a set of values based on the set of spectral metrics to obtain a first result, the first trained model trained on a first set of training samples for first particles of interest and a second set of training samples for second particles of interest, the first particles of interest including at least a first type of the first particles of interest and a second type of the first particles of interest;

applying a second trained model to at least one of the set of spectral metrics and the set of values to obtain a second result, the second trained model being different than the first trained model and trained on a third set of training samples for the first type of the first particles of interest and a fourth set of training samples for the second type of the first particles of interest;

based on at least one of the first result and the second result, determining either a positive particle of interest detection or a negative particle of interest detection for at least one of the first particles of interest, the first type of the first particles of interest, and the second type of the first particles of interest for the sample;

generating a particle of interest detection notification that indicates either the positive particle of interest detection or the negative particle of interest detection; and providing the particle of interest detection notification.

12. The method of claim 11 wherein the sample is at least one of a sample of a food processing byproduct, a sample from a person, and an environmental sample, and at least one of the first particles of interest and the second particles of interest includes at least one of a foodborne pathogen, pathogen that infects humans or animals, and an environmental particle of interest.

13. The method of claim 11, further comprising normalizing each spectral metric in the set of spectral metrics to be between zero, inclusive, and one, inclusive, to obtain the set of values, and wherein applying the first trained model to at least one of the set of spectral metrics and the set of values based on the set of spectral metrics to obtain the first result includes applying the first trained model to the set of values.

14. The method of claim 11, further comprising:

training a first model on the first set of training samples for the first particles of interest and the second set of training samples for the second particles of interest to obtain the first trained model; and training a second model on the third set of training samples for the first type of the first particles of interest and the fourth set of training samples for the second type of the first particles of interest to obtain the second trained model.

15. The method of claim 11 wherein the first set of training samples includes a first subset of training samples containing the first particles of interest at a first concentration and a second subset of training samples containing the first particles of interest at a second concentration different from the first concentration, and wherein the second set of training samples includes a third subset of training samples containing the second particles of interest at a third concentration and a fourth subset of training samples containing the second particles of interest at a fourth concentration different from the third concentration.

16. A system comprising at least one processor and memory containing executable instructions, the executable instructions being executable by the at least one processor to:

receive data, the data including a set of spectral metrics, the data from an apparatus that obtains the set of spectral metrics based on interactions of electromagnetic radiation with a sample;

apply a first trained model to at least one of the set of spectral metrics and a set of values based on the set of spectral metrics to obtain a first result, the first trained model trained on a first set of training samples for first particles of interest and a second set of training samples for second particles of interest, the first particles of interest including at least a first type of the first particles of interest and a second type of the first particles of interest;

apply a second trained model to at least one of the set of spectral metrics and the set of values to obtain a second result, the second trained model being different than the first trained model and trained on a third set of training samples for the first type of the first particles of interest and a fourth set of training samples for the second type of the first particles of interest;

based on at least one of the first result and the second result, determine either a positive particle of interest detection or a negative particle of interest detection for at least one of the first particles of interest, the first type of the first particles of interest, and the second type of the first particles of interest for the sample;

generate a particle of interest detection notification that indicates either the positive particle of interest detection or the negative particle of interest detection; and provide the particle of interest detection notification.

17. The system of claim 16 wherein the sample is at least one of a sample of a food processing byproduct, a sample from a person, and an environmental sample, and at least one of the first particles of interest and the second particles of interest includes at least one of a foodborne pathogen, a pathogen that infects humans or animals, and an environmental particle of interest.

18. The system of claim 16, the executable instructions being further executable by the at least one processor to normalize each spectral metric in the set of spectral metrics to be between zero, inclusive, and one, inclusive, to obtain the set of values, and wherein the executable instructions to apply the first trained model to at least one of the set of spectral metrics and the set of values based on the set of spectral metrics to obtain the first result includes executable instructions being executable by the at least one processor to apply the first trained model to the set of values.

19. The system of claim 16, the executable instructions being further executable by the at least one processor to:

train a first model on the first set of training samples for the first particles of interest and the second set of training samples for the second particles of interest to obtain the first trained model; and train a second model on the third set of training samples for the first type of the first particles of interest and the fourth set of training samples for the second type of the first particles of interest to obtain the second trained model.

20. The system of claim 16 wherein the first set of training samples includes a first subset of training samples containing the first particles of interest at a first concentration and a second subset of training samples containing the first particles of interest at a second concentration different from the first concentration, and wherein the second set of training samples includes a third subset of training samples containing the second particles of interest at a third concentration and a fourth subset of training samples containing the second particles of interest at a fourth concentration different from the third concentration.

* * * * *